United States Patent [19]

Kume et al.

[11] Patent Number: 5,523,414

[45] Date of Patent: Jun. 4, 1996

[54] METHOD FOR PRODUCTION OF MALEINAMIC ACID, ESTERS THEREOF, AND MALEINIMIDE

[75] Inventors: Yasuhiro Kume; Takehiko Morita; Kazuo Kishino; Yuichi Kita; Hitoshi Kanei, all of Hyogo, Japan

[73] Assignee: Nippon Shokubai Co., Ltd., Osaka, Japan

[21] Appl. No.: 239,609

[22] Filed: May 9, 1994

[30] Foreign Application Priority Data

| Oct. 6, 1993 | [JP] | Japan | 5-250512 |
| Apr. 27, 1994 | [JP] | Japan | 6-090002 |
| Apr. 27, 1994 | [JP] | Japan | 6-090003 |
| Apr. 28, 1994 | [JP] | Japan | 6-090947 |

[51] Int. Cl.$^6$ .............................................. C07D 207/452
[52] U.S. Cl. ............................................ 548/548; 548/549
[58] Field of Search ............................................. 548/548

[56] References Cited

U.S. PATENT DOCUMENTS

| 3,899,509 | 8/1975 | Riemenschneider | 260/3265 EM |
| 5,087,705 | 2/1992 | Okada et al. | 548/548 |

FOREIGN PATENT DOCUMENTS

| 1934791 | 1/1971 | Germany . |
| 4935325 | 8/1972 | Japan . |
| 50-126659 | 3/1974 | Japan . |
| 0082620 | 12/1982 | Japan . |
| 60-188367 | 2/1985 | Japan . |
| 62-215563 | 3/1986 | Japan . |
| 62-235740 | 9/1987 | Japan . |
| 03118362 | 9/1989 | Japan . |
| 03184956 | 8/1990 | Japan . |
| 03173866 | 9/1990 | Japan . |
| 04221365 | 12/1990 | Japan . |
| 04290868 | 3/1991 | Japan . |
| 4290868 | 3/1991 | Japan . |
| 04281324 | 10/1992 | Japan . |
| 06184105 | 12/1992 | Japan . |

*Primary Examiner*—David B. Springer
*Attorney, Agent, or Firm*—Omri M. Behr; Matthew J. McDonald

[57] ABSTRACT

In the production of an N-unsubstituted maleinimide by the ring-closing alcohol-removing treatment of an N-unsubstituted maleinamic ester for conversion into an imide, an acid catalyst or a mono(cyclo)alkyl sulfuric ester is used for the reaction. In this case, the alcohol concentration in the reaction solution is preferable to be adjusted to a low level. By using a maleinamic acid and an alcohol in conjunction with an inert solvent and an acid catalyst, a mixture of maleinamic acid with an acid catalyst, or a mono(cyclo)alkyl sulfuric ester, a corresponding maleinamic ester is obtained. In a method for the production of a maleinamic acid by the reaction of maleic anhydride with ammonia in an inert solvent, the maleinamic acid is obtained by placing a solution of the maleic anhydride in the inorganic solvent in a reactor, meanwhile introducing ammonia gas into the empty space part of the reactor, and allowing the ammonia gas to be absorbed in the solution through the surface of contact between the solution and the ammonia gas. Further, in the method for the production of a maleinamic acid by the reaction of maleic anhydride with ammonia in an inert solvent, the reaction is carried out while the concentration of the maleic anhydride in the reaction solution is kept at a level of not more than 10% by weight or the ammonia concentration in the reaction solution is kept at a level of not less than 0.001% by weight.

11 Claims, 1 Drawing Sheet

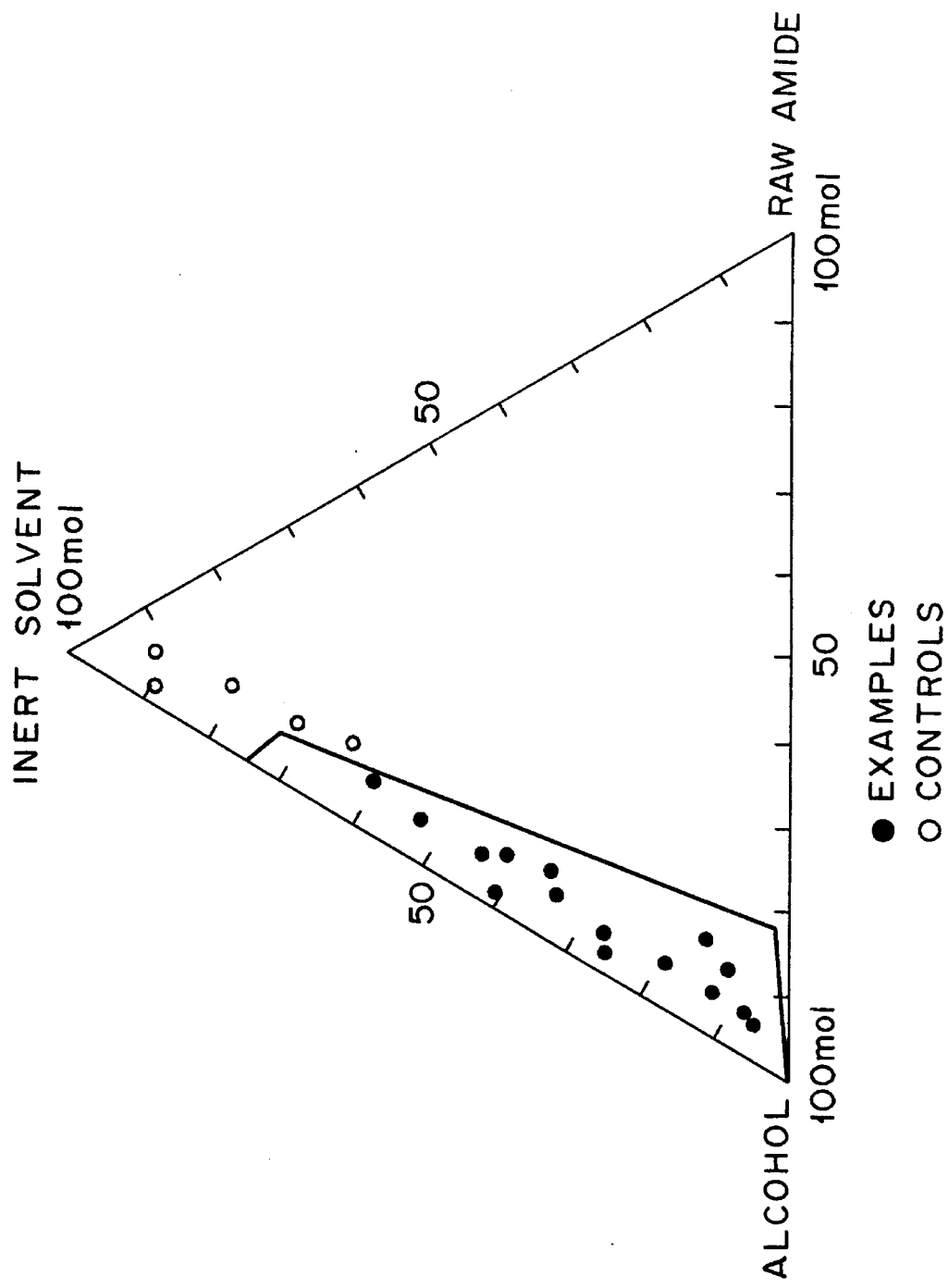

METHOD FOR PRODUCTION OF MALEINAMIC ACID, ESTERS THEREOF, AND MALEINIMIDE

DESCRIPTION

1. Technical Field

This invention relates to a method for the production of maleinamic acid, esters thereof, and maleinimide. More particularly, it relates to a method for the production of maleinamic acid from maleic anhydride and ammonia, a method for the production of maleic esters by the reaction of a maleinamic acid with an alcohol, and a method for the production of malainimides from malainamic esters as the starting material.

2. Background Art

Maleinamic acid is a compound which is useful as the raw material for the production of maleinamic esters, for example. Maleinamic esters are compounds which are useful as the raw materials for thermoplastic resins demanding heat resistance and also useful as the intermediates for medicines and agricultural pesticides. Then, maleinimides are compounds which are useful as the raw material for thermoplastic resins demanding heat resistance and also useful as the intermediates for medicines and agricultural pesticides.

It is known that a maleinamic acid is obtained by the reaction of maleic anhydride with ammonia, specifically by passing ammonia through maleic anhydride in an inert solvent. It is also known that a maleinamic acid and an alcohol, on being subjected to thermal dehydration, produce a corresponding maleinamic esters.

JP-A-49-35,325 discloses a method for producing a maleinamic acid of high purity by causing maleic anhydride to react with ammonia of an equimolar amount or less in an inert solvent and then allowing the reaction to continue while deterring passage of ammonia. This method, however, has the problem of production that when ammonia gas is blown into the solution of maleic anhydride in the inert solvent to produce the maleinamic acid, crystals of maleinamic acid copiously precipitate in the neighborhood of an orifice introducing the ammonia gas into the reaction solution and eventually block this orifice to render it difficult to continue the reaction. Further, since the maleinamic acid obtained by this method has contained therein the unaltered ammonia which persisted in the crystals mentioned above, the production of a maleinamic ester by the esterification of the maleinamic acid with an alcohol entails the problem of requiring the maleinamic acid to be refined in advance of the esterification.

It is also known in the art that an N-substituted maleinamic acid, on reacting with an alcohol in the presence of sulfuric acid or an ion-exchange resin, produces a corresponding N-substituted maleinamic ester.

JP-A-03-184,956, for example, discloses a method for producing an N-aryl maleinimide from an N-aryl maleinamic acid and an alcohol via an N-aryl maleinamic ester. This method is described as producing an N-aryl maleinamic ester by causing the corresponding raw-material N-aryl maleinamic acid to react with about 3 times its molar quantity of an alcohol in the presence of sulfuric acid as a catalyst while removing by distillation the formed water in conjunction with an azeotropic solvent from the system.

Further, JP-04-290,868 discloses the production of an N-substituted maleinamic ester by the reflux of a corresponding alcohol solvent instead of the use of an azeotropic solvent.

When the method of JP-A-03-184,956 mentioned above is used for the production an N-unsubstituted or -substituted maleinamic ester, however, the corresponding maleinamic ester is obtained at an extremely low rate of conversion or in a very small amount because the reaction gives rise to such by-products as the hydrolyzate in a large amount. If the reaction time is elongated for the sake of enhancing the conversion, the selectivity of the reaction will be degraded and the yield lowered.

JP-A-04-221,365 further discloses a method for producing an N-methyl maleinamic ester from an N-methyl maleinamic acid and an alcohol. In a working example of this method, an N-methyl maleinamic ester is obtained by causing the corresponding raw-material N-methyl maleinamic acid to react with three times its molar quantity of an alcohol in the presence of sulfuric acid as a catalyst while removing by distillation the formed water in conjunction with an azeotropic solvent from the system. The yield of this reaction is very low.

Despite the fact that maleinamic esters are very useful compounds as described above, no ideal technique for their synthesis has been established to date.

Concerning the production of maleinimides, numerous methods have been known to the art. U.S. Pat. No. 3,899,509, for example, discloses a method for continuous recycling production of a malainimide by the reaction of maleic acid or hydrocarbon-mixed maleic acid with ammonia in a gaseous phase in the presence of a dehydration catalyst. European Patent No. 82,620 discloses a method for producing maleinimide by the ammoxidation of 1,3-butadiene with ammonia in the presence of an oxidation catalyst formed of a variable-valency metal oxide and JP-A-60-188,367 discloses a method for producing a maleinimide by the oxidative dehydrogenation of succinimide in the presence of a specific catalyst. These methods are invariably at a disadvantage in attaining the production only in low yields, involving highly complicated procedures, and entailing high costs of production. Besides, a method which obtains a maleinimide by causing furan, cyclopentadiene, etc. to react on maleic anhydride thereby forming Diels-Alder adduct, treating the adduct with ammonia thereby converting it into an imide compound, and then thermally decomposing the imide compound is known to the art. This method, however, is unfit for producing maleinimide on a commercial scale because of the complicated process involved.

The most ordinary method for producing a maleinimide comprises the dehydrocyclization of a maleinamic acid by use of a dehydrator. German Patent No. 1,634,791 discloses a method for producing a malainimide by use of orthophosphoric acid as the dehydrator. This method, however, has drawbacks such as poor yield. A method which is disclosed in JP-A-50-126,659 uses acetyl chloride, benzoyl chloride, thionyl chloride, phosphorus pentoxide, etc. as a dehydrator. These dehydrators invariably are handled with difficulty because they are highly reactive with water and are highly corrosive as well. This method, therefore, is unfit for commercial operation because of poor workability and high cost of equipment. JP-A-64-7,148 discloses a method for producing a maleinimide by use of cyanuric chloride as a dehydrator and N,N-dimethyl formamide as a solvent. This method does not deserve to be rated as suitable for commercial operation because it is expensive to operate and it uses such toxic substances as cyanuric chloride and dimethyl formamide. Further, since such a non-protonic polar solvent as dimethyl formamide has a high boiling point, this method is at a disadvantage in encountering difficulty in the removal of the solvent from the produced maleinimide.

As regards the production of N-substituted maleinimide derivatives, JP-A-62-215,563, for example, discloses a method for producing an N-substituted maleinimide by causing a maleic monoester to react with an isocyanate compound thereby forming a maleinamic monoester and then heating the maleinamic monoester under a high degree of vacuum thereby effecting the ring-opening conversion into an imide by removal of an alcohol. This method, however, is completely disadvantageous from the commercial point of view because the raw-material isocyanate compound is relatively expensive and because the reaction for the removal of the alcohol requires such a high degree of vacuum as $10^{-3}$ to $10^{-5}$ mmHg and inevitably necessitates installation of a vacuum pump of high performance capable of realizing the vacuum condition mentioned above and accessorial devices therefor and incurs a huge cost of equipment. Incidentally, in this method, the alcohol which is formed during the alcohol-removing reaction of the maleinamic monoester is separated as condensed by means of a trap and the reaction product, namely the N-substituted maleinimide compound, is separated by having the reaction solution dispersed in water and allowing the reaction product to sediment in the dispersion (refer to Example 1 cited in the specification).

JP-A-03-118,362 discloses a method for producing an N-substituted maleinimide by subjecting an N-substituted maleinamic monoester to an alcohol-removing reaction in the presence of an acid catalyst and superheated steam thereby effecting the ring-opening conversion thereof into an imide. This method, however, is economically disadvantageous over the method which effects the alcohol-removing reaction simply by application of heat in respect that it is required to use superheated steam. This method can be implemented batchwise or continuously and, in the case of the batchwise operation, attains the alcohol-removing reaction by introducing the mixture of the maleinamic ester with the acid catalyst into the reactor and exposing them therein to the superheated steam (refer to the passage in the left upper column, page 5 of the specification). In the continuous operation, this method obtains the N-substituted maleinimide by removing the reaction mixture together with steam from the reactor and cooling them thereby separating the product (refer to Example 1 cited in the specification).

JP-A-03-173,866 discloses a method for producing an N-substituted maleinimide by heating a mixture consisting of an N-maleinamic monoester, an acid catalyst, an inert solvent, and an alcohol thereby effecting the alcohol-removing reaction and the consequent ring-opening conversion into an imide. In this method, the alcohol-removing reaction is effected by heating and stirring the mixture in a reflux and then the reaction solution is cooled first to separate the water phase (acid catalyst) and then to separate the N-substituted maleinimide from the organic phase (refer to Example 1 cited in the specification).

In JP-A-03-184,956 is disclosed a method for producing an N-substituted maleinimide by esterifying an N-substituted maleinamic acid with an alcohol in the presence of an acid catalyst and heating the produced N-substituted maleinamic ester in an inert solvent in the presence of an acid catalyst thereby effecting the alcohol-removing reaction. Particularly, the production of the N-substituted maleinimide by this method is characterized by adding a polymerization inhibitor to the reaction system during the process of the ring-opening conversion into an imide by the alcohol-removing reaction. In the process of the ring-opening conversion into an imide according to this method, the formed alcohol is removed together with the used solvent by azeotropic distillation and the solvent consequently lost is replenished from time to time to keep constant the solvent supply in the reaction system (refer to the right lower column, page 6 of the specification). Further, in this method, the reaction solution is cooled and then the cooled reaction solution is washed with water to separate the water layer (acid catalyst) and then effect the separation of the N-substituted maleinimide from the remaining organic layer (refer to Example 1 cited in the specification).

JP-A-04-221,365 discloses a method for producing an N-substituted maleinimide by subjecting an N-substituted maleinamic monoester in a solvent to the ring-opening conversion into an imide in the presence of a catalyst which is formed of the alkali metal salt of an inorganic acid and/or an organic acid. In this method, the reaction is carried out at room temperature (25° C.), the catalyst is separated by filtration after the reaction is completed, and the produced N-substituted maleinimide is separated from the remaining reaction solution (refer to Example 1 cited in the specification).

The present inventors have applied the methods disclosed in JP-03-184,956, JP-A-04-221,365, and JP-A-04-290,868 mentioned above severally to the production of a maleinimide by use of sulfuric acid as an imide conversion catalyst as aimed at by the present inventors, to find that N-substituted maleinamic esters easily undergo the alcohol-removing reaction in the presence of such a sulfuric acid catalyst as is taught in the publications known to the art and produce corresponding N-substituted maleinimides, whereas maleinamic esters, on being subjected to the reaction under the same conditions, inevitably give birth to such by-products as maleic acid, maleic diester, and maleic monoester and, therefore, hardly produce maleinimides aimed at. Despite the wide-spread appreciation of maleinimides as useful compounds, the methods heretofore proposed for the production of these compounds are never capable of producing the compounds in a high yield.

An object of this invention, therefore, is to provide a novel method for the production of maleinamic acids, esters thereof, and maleinimides.

Another object of this invention is to provide a method for producing a maleinamic acid of high purity in a high yield from maleic anhydride and ammonia.

A further object of this invention is to provide a method for producing an N-unsubstituted or N-substituted maleinamic ester expeditiously in a high yield with high selectivity from an N-unsubstituted or N-substituted maleinamic acid and an alcohol.

Still another object of this invention is to provide a method for producing a maleinimide expeditiously in a high yield with high selectivity from a maleinamic ester.

DISCLOSURE OF THE INVENTION

The various objects mentioned above are accomplished by a method for the production of a maleinimide, characterized in that the production is attained by heating a maleinamic ester compound represented by the general formula (1):

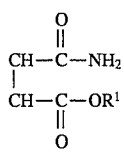

(1)

wherein $R^1$ is an alkyl group of 1 to 8 carbon atoms or a cycloalkyl group of 3 to 8 carbon atoms, in an inert organic solvent in conjunction with an acid catalyst or a mono(cyclo)alkyl sulfuric ester represented by the general formula (2):

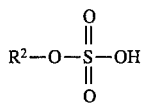

(2)

wherein $R^2$ is an alkyl group of 1 to 8 carbon atoms or a cycloalkyl group of 3 to 8 carbon atoms, thereby effecting an alcohol-removing ring-closing reaction.

This invention also contemplates the aforementioned method, wherein the concentration of the alcohol in the reaction system is retained at not more than 3% by weight. This invention contemplates the method, wherein the amount of the acid catalyst to be used is in the range of from 0.01 to 2 times the molar quantity of the maleinamic ester. This invention further contemplates the method, wherein the acid catalyst is obtained by depositing at least one member selected from the group consisting of sulfuric acid, sulfuric anhydride, sulfonic acid, phosphoric acid, phosphorous acid, and hypophosphorous acid on a solid carrier. This invention contemplates the method, wherein the catalyst is a mono-(cyclo)alkyl sulfuric ester represented by the general formula (2). This invention further contemplates the method, wherein $R^1$ and $R^2$ are identical with each other.

The various objects mentioned above are also accomplished by a method for producing a maleinimide by heating a maleinamic ester represented by the general formula (1) thereby effecting an alcohol-removing reaction and the consequent ring-closing conversion into an imide, characterized in that the reaction is carried out while the formed alcohol and the produced maleinimide are expelled by distillation out of the reaction system.

This invention also contemplates the aforementioned method, wherein the alcohol-removing ring-closing reaction is carried out while the alcohol concentration in the reaction system is kept at a level of not more than 3% by weight.

The various objects mentioned above are further accomplished by a method for the production of a maleinamic ester represented by the general formula (6):

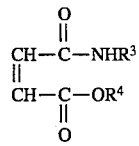

(6)

wherein $R^3$ is hydrogen atom, an alkyl group of 1 to 8 carbon atoms, or a cycloalkyl group of 3 to 8 carbon atoms and $R^4$ is an alkyl group of 1 to 8 carbon atoms or a cycloalkyl group of 3 to 8 carbon atoms, characterized in that the production is attained by causing the reaction of a maleinamic acid represented by the general formula (3):

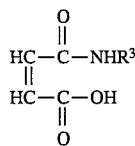

(3)

wherein $R^3$ has the same meaning as defined above, with an alcohol represented by the general formula (4):

$R^4$—OH (4)

wherein $R^4$ has the same meaning as defined above, in the presence of an inert solvent and an acid catalyst, a mixture of the maleinamic acid with an acid catalyst, or a mono(cyclo)alkyl sulfuric ester represented by the general formula (5):

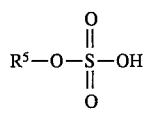

(5)

wherein $R^5$ is an alkyl group of 1 to 8 carbon atoms or a cycloalkyl group of 3 to 8 carbon atoms.

This invention also contemplates the aforementioned method, wherein the ratio of the alcohol to the maleinamic acid is not less than 5 by molar equivalent weight, the ratio of the inert solvent to the maleinamic acid is not less than 0.1 by molar equivalent weight, the ratio of the inert solvent to the alcohol is not more than 3 by molar equivalent weight, and the reaction temperature is in the range of from 10° to 100° C. This invention further contemplates the method, wherein the acid catalyst is a sulfonic acid type catalyst, a phosphoric acid type catalyst, or an acidic ion-exchange resin. This invention also contemplates the method, wherein the sulfonic acid type catalyst is at least one member selected from the group consisting of sulfuric acid, sulfuric anhydride, aryl sulfonic acid, alkyl sulfonic acid, mono(cyclo)alkyl sulfonic esters, and acidic ion-exchange resins. This invention contemplates the method, wherein the sulfonic acid type catalyst is sulfuric acid. This invention also contemplates the method, wherein the catalyst is a mixture of the maleinamic acid with the sulfonic acid type catalyst. This invention further contemplates the method, wherein the sulfonic acid catalyst is sulfuric acid. This invention further contemplates the method, wherein the catalyst is a mono-(cyclo)alkyl sulfuric ester represented by the general formula (5). This invention contemplates the method, wherein $R^3$ and $R^4$ are identical with each other. This invention further contemplates the method, wherein the inert solvent is capable of forming an azeotropic mixture with the alcohol.

The various objects mentioned above are accomplished by a method for producing a maleinamic acid by the reaction of maleic anhydride with ammonia in an inert solvent, characterized in that the production is attained by placing a solution of the maleic anhydride in the inert solvent in a reactor, meanwhile introducing ammonia gas into the empty space part of the reactor, allowing ammonia to be absorbed in the solution through the surface of contact between the solution and the ammonia gas, and enabling the absorbed ammonia to react with the maleic anhydride. The various objects mentioned above are also accomplished by a method for producing a maleinamic acid by the reaction of maleic anhydride with ammonia in an inert solvent, characterized in that the production is attained by causing the reaction to proceed while supplying the maleic anhydride and ammonia to the reaction solution so that the maleic anhydride concentration in the reaction solution may remain at a leve of not more than 10% by weight.

The various objects mentioned above are further accomplished by a method for producing a maleinamic acid by the reaction of maleic anhydride with ammonia in an inert solvent, characterized in that the production is attained by causing the reaction to proceed while keeping the ammonia concentration in the reaction solution at a level of not less than 0.01% by weight.

BRIEF DESCRIPTION OF DRAWINGS

FIG. 1 represents the scope of this invention in terms of the relation of maleinamic acid, alcohol, and inert solvent.

BEST MODE FOR CARRYING OUT THE INVENTION

We have made a diligent study in search of the cause for a notable decrease of yield which is encountered during the production of a maleinimide by the aforementioned alcohol-removing reaction of a corresponding maleinamic ester, to find that the amide group which is destitute of a substituting group has one more active hydrogen atom in the molecular unit thereof than the amide group which is possessed of a substituting group and, therefore, imparts an appreciably increased polarity to the molecule of a compound incorporating the amide group and gives rise to prominent difference in the solubility of the compound in an organic solvent or in the reactivity thereof equivalent to a functional group.

After further continuing this study, we have unveiled the fact that the amide group destitute of a substituting group manifests high reactivity to an acid of relatively high strength and readily decomposes on contact with the acid and consequently the fact that this susceptibility to decomposition is responsible for the difference in reactivity between the group of N-substituted compounds such as N-substituted maleinamic esters and N-substituted maleinimides and the group of N-unsubstituted compounds such as maleinamic esters and maleinimides.

As described above, the N-substituted compounds and the N-unsubstituted compounds are entirely different compounds. When known methods for the production of N-substituted maleinimides are simply utilized for the production of a maleinimide, they are never capable of yielding satisfactory results.

The maleinamic esters represented by the general formula (1) to be used in this invention are produced by the well-known method from an alcohol and a maleinamic acid. $R^1$ in the formula is an alkyl group of 1 to 8, preferably 3 to 6, carbon atoms or a cycloalkyl group of 3 to 8, preferably 5 to 7, carbon atoms. As typical examples of $R^1$, methyl group, ethyl group, n-propyl group, isopropyl group, n-butyl group, isobutyl group, sec-butyl group, t-butyl group, amyl group, sec-amyl group, isoamyl group, n-hexyl group, isohexyl group, n-heptyl group, n-octyl group, 2-ethylhexyl group, cycloheptyl group, cyclopentyl group, and cyclohexyl group may be cited.

As typical examples of the maleinamic esters represented by the general formula (1) to be used as the starting material, maleinamic methyl ester, maleinamic ethyl ester, maleinamic n-propyl ester, maleinamic isopropyl ester, maleinamic n-butyl ester, malainamic isobutyl ester, maleinamic sec-butyl ester, maleinamic t-butyl ester, maleinamic amyl ester, maleinamic sec-amyl ester, maleinamic isoamyl ester, maleinamic n-hexyl ester, maleinamic isohexyl ester, maleinamic 2-ethylhexyl ester, maleinamic cyclopentyl ester, maleinamic cyclohexyl ester, and maleinamic cycloheptyl ester may be cited.

The acid catalyst to be used in this invention is not particularly critical. Any of the acid catalysts which are generally used in the reactions of this class may be used. Such sulfonic acids as sulfuric acid, sulfuric anhydride, methane sulfonic acid, p-toluene sulfonic acid, and benzene sulfonic acid and such phosphoric acids as orthophosphoric acid, metaphosphoric acid, pyrophosphoric acid, phosphorous acid, and hypophosphorous acid are particularly desirable typical examples. The acid catalyst is desired to be used as deposited on a solid carrier as by reason of great ease with which it is separated from the reaction solution.

As the solid carrier mentioned above, either an inorganic carrier or an organic carrier may be used. As typical examples of the inorganic carrier, such natural minerals as kaolines, clay, talc, chalk, quartz, bentonite, montmorillonite, and diatomaceous earth and such natural rocks as silicic acid, silicates, alumina, activated carbon, gypsum, red oxide, titanium dioxide, silica, silica-alumina, and zirconium oxide may be cited. As typical examples of the organic carrier, polyfluorocarbon, polystyrene, and phenol resin may be cited. Among the various simple solid substances mentioned above, such porous substances as diatomaceous earth and silica gel are used particularly advantageously in respect that they yield ideal results. As respects the form of such a solid carrier, powder, beads, honeycombs, etc. may be suitably selected. The amount of the acid catalyst to be deposited on the solid carrier is generally in the range of from 0.5 to 500% by weight, preferably from 5 to 200% by weight, based on the amount of the solid carrier, though it is variable more or less depending on the kind of the simple solid substance to be used.

The method for depositing the acid catalyst on the solid carrier is not particularly critical. Any of the methods which are generally used for the deposition of this nature may be used. Methods resorting to impregnation, spraying, etc. may be cited as typical examples. The acid catalyst may be directly deposited on the solid carrier or it may be solved in an organic solvent or water and then deposited in the form of a solution on the solid carrier. The mode of use of the carried catalyst is not particularly critical. The carried catalyst may be prepared in a pulverized form and used as suspended in a stirring type reaction kettle, for example. Otherwise, it may be prepared in a granular form and packed in a fixed bed and used in a flow reactor.

The amount of the acid catalyst or the mono(cyclo)alkyl sulfuric ester to be used (as acid component when it is used as deposited on a solid carrier) is in the range of from 0.01 to 4, preferably 0.05 to 2, times the molar quantity of the maleinamic ester being used as the raw material. If this amount is less than 0.01 times the molar quantity, the reaction will not easily proceed. Conversely, if the amount exceeds 4 times the molar quantity, the excess will tend to cause secondary reactions.

Then, $R^2$ of the mono(cyclo)alkyl sulfuric ester represented by the general formula (2) is an alkyl group of 1 to 8, preferably 3 to 6, carbon atoms or a cycloalkyl group of 3 to 8, preferably 5 to 7, carbon atoms. As typical examples of $R^2$, methyl group, ethyl group, n-propyl group, isopropyl group, n-butyl group, isobutyl group, sec-butyl group, t-butyl group, amyl group, sec-amyl group, isoamyl group, n-hexyl group, isohexyl group, n-heptyl group, n-octyl group, 2-ethylhexyl group, cyclopentyl group, cyclohexyl group, and cycloheptyl group may be cited.

As typical examples of the mono(cyclo)alkyl sulfuric esters represented by the general formula (2), monomethyl sulfuric esters, monoethyl sulfuric esters, mono-n-propyl sulfuric esters, monoisopropyl sulfuric esters, mono-n-butyl sulfuric esters, monoisobutyl sulfuric esters, mono-sec-butyl sulfuric esters, mono-tert-butyl sulfuric esters, monoamyl sulfuric esters, mono-sec-amyl sulfuric esters, monoisoamyl sulfuric esters, mono-n-hexyl sulfuric esters, monoisohexyl sulfuric esters, mono-n-heptyl sulfuric esters, mono-n-octyl sulfuric esters, mono-2-ethylhexyl sulfuric esters, monocyclopentyl sulfuric esters, monocyclohexyl sulfuric esters, and monocyclobutyl sulfuric esters may be cited.

The mono(cyclo)alkyl sulfuric acids contemplated by this invention may embrace sulfuric acid, sulfuric anhydride, p-toluene sulfonic acid, benzene sulfonic acid, methyl sulfonic acid, ethyl sulfonic acid, propyl sulfonic acid, butyl sulfonic acid, octyl sulfonic acid, salts of maleinamic acid with sulfuric acid, acidic ion-exchange resins, etc.

As the reaction solvent, any of the inert organic solvents which are in popular use can be used. These inert organic solvents may be used either singly or in the form of a combination of two or more members. As typical examples of the reaction solvent, diethylene glycol dimethyl ether, ethylene glycol dimethyl ether, acetone, methylethyl ketone, diethyl ether, dioxane, tetrahydrofuran, sulforan, dimethyl sulfoxide, dichloromethane, chloroform, benzene, toluene, xylene, pentane, hexane, cyclopentane, and cyclohexane may be cited. Among other inert organic solvents mentioned above, toluene and xylene prove particularly desirable.

The amount of the reaction solvent to be used is preferable to be in the range of from 1 to 50 parts by weight, preferably from 2 to 20 parts by weight, based on 1 part by weight of the maleinamic ester represented by the general formula (1) to be used as the starting material, from the viewpoint of satisfying economic conditions.

If the temperature of the reaction is unduly high, the reaction will induce secondary reactions. If it is unduly low, the reaction will not proceed. The reaction, therefore, is carried out at a temperature in the range of from 20° to 200° C., preferably from 70° to 180° C. The reaction may be carried out under normal pressure, an increased pressure, or a reduced pressure so long as the temperature of the reaction falls in the range specified above. The reaction time is in the range of from 0.5 to 20 hours, preferably from 2 to 10 hours, though it is variable more or less depending on the concentration of the reaction solution.

In the reaction of this invention, any of the polymerization inhibitors which are in popular acceptance may be used. The kind of the polymerization inhibitor is not particularly critical. As typical examples of the polymerization inhibitor, phenol, methoxy phenol, t-butyl catechol, hydroquinone, t-butyl hydro-quinone, dilauryl thiodipropionate, distearyl thiodipropionate, sodium diethyl dithiocarbamate, sodium diethyl dithiocarbamate, copper dibutyl dithiocarbamate, zinc dibutyl dithiocarbamate, sodium salicylate, phenothiazine, 2-mercaptobenzimidazole, and triphenyl phosphite may be cited.

The reaction for conversion into an imide in the present invention is intended for the removal of an alcohol. It can be made to proceed advantageously, therefore, by continuing the reaction while causing the formed alcohol and the solvent to be expelled simultaneously by distillation. Thus, $R^1$ of the general formula (1) and $R^2$ of the general formula (2) are preferable to be identical with each other because the alcohols to be formed are identical with each other.

The alcohol which has been distilled out of the system in conjunction with the solvent may be separated from the solvent and used again in the raw material, while the solvent which remains after the separation of the alcohol may be returned for reuse to the reaction system.

As regards the addition of the maleinamic ester, the reaction solvent, the mono(cyclo)alkyl sulfuric ester, and the polymerization initiator to the reaction system in the method of this invention, the order of their addition is not particularly critical. Since ideal stirring of the reaction system is indispensable for smooth progress of the reaction, it is preferable to add first the reaction solvent, then the mono-(cyclo)alkyl sulfuric ester, and thereafter the polymerization inhibitor, and the maleinamic ester. The maleinamic ester may be added continuously, batchwise, or semi-batchwise. In a particularly preferable mode of embodiment of this invention, the kind of reaction solvent to be used in the reaction under discussion is selected so as to be identical with that of the organic solvent which has been specifically used in the production of the maleinamic ester as the raw material.

In this invention, the alcohol which is formed in the reaction is expelled together with the inert organic solvent by distillation from the reaction system. The distillate thus produced can be collected by any of the conventional methods which are represented by cooling. The alcohol which has been expelled in conjunction with the inert organic solvent by distillation from the reaction system can be separated from the inert organic solvent and used again in, the raw material, while the inert organic solvent which remains after the separation of the solvent can be returned for reuse to the reaction system.

In accordance with the method of this invention, the reaction for removal of alcohol is preferable to be carried out while the concentration in the reaction system of the alcohol formed in consequence of the reaction for removal of alcohol, namely the alcohol concentration in the reaction solution, is kept adjusted meanwhile at a level of not more than 3% by weight, preferably not more than 1% by weight. For the sake of adjusting the alcohol concentration in the reaction solution in the range specified above, it suffices to select suitably the reaction temperature and expel the formed alcohol together with the used inert organic solvent by distillation from the reaction system.

The reaction for removal of alcohol to be carried out in this invention is made to proceed by heating. It may use a catalyst for the purpose of exalting the reaction velocity. This catalyst may be any of the catalysts which are generally adopted for reactions intended for removal of an alcohol. As typical examples of the catalyst, inorganic acids such as hydrochloric acid, nitric acid, carbonic acid, and phosphoric acid and metal salts thereof, organic acids such as acetic acid, maleic acid, fumaric acid, succinic acid, and phthalic acid and metal salts thereof, composites having such acid components deposited on inert carriers, and ion-exchange resins may be cited besides the acid catalysts and the mono(cyclo)alkyl sulfuric esters.

The maleinimide which is produced as described above is subjected to radical homopolymerization or copolymerization to give rise to a heat-resistant thermoplastic resin. This compound is also useful as an intermediate for medicines, agricultural pesticides, etc.

We have made an elaborate study in search of the conditions for producing an N-unsubstituted or N-substituted alkyl maleinamic ester in a high yield with a due consideration to the series of chemical and physical properties of the unsubstituted compounds or N-substituted alkyl compounds mentioned above, to find that the N-unsubstituted or N-substituted alkyl maleinamic ester is obtained in a highly satisfactory yield by controlling the acid strength of the acid catalyst to be used in the production. This invention has been perfected as a result.

According to our knowledge, sulfuric acid, sulfuric anhydride, aryl sulfonic acid, a mixture of alkyl sulfonic acids, or a monoalkyl sulfuric acid exhibits a specific catalytic activity to maleinamic acid or an N-alkyl maleinamic acid in the synthesis of the maleinamic ester or the N-alkyl maleinamic ester.

This invention has realized the production of a corresponding maleinamic ester in a conspicuously high yield.

$R^3$ in the maleinamic acid represented by the general formula (3) to be used in this invention is hydrogen atom or an alkyl group of 1 to 8, preferably 3 to 7, carbon atoms. The alkyl group just mentioned may contain a substituting group. The substituting groups which are allowed to be contained in the alkyl group include halogen atoms, hydroxyl group, cyano group, nitro group, carbonyl group, sulfonyl group, and alkoxy group, for example. As typical examples of the maleinamic acids of the general formula (3), maleinamic acid, N-methyl maleinamic acid, N-ethyl maleinamic acid, N-n-propyl maleinamic acid, N-isopropyl maleinamic acid, N-n-butyl maleinamic acid, N-sec-butyl maleinamic acid, N-isobutyl maleinamic acid, N-tert-butyl maleinamic acid, N-n-hexyl maleinamic acid, N-octyl maleinamic acid, N-decyl maleinamic acid, N-dodecyl maleinamic acid, and N-octadecyl maleinamic acid may be cited. These maleinamic acids can be produced by the well-known method from ammonia or a primary amine and maleic anhydride.

The alcohol represented by the general formula (4) to be used in this invention may be in a saturated form or an unsaturated form, the former being preferable over the latter. Further, the alcohol may be in a linear or a cyclic structure. $R^4$ specifically embraces alkyl groups of 1 to 8, preferably 3 to 7, carbon atoms and cycloalkyl groups of 3 to 7, preferably 5 to 7, carbon atoms. As typical examples of the alcohol of the general formula (4), primary alcohols such as methanol, ethanol, n-propanol, n-butanol, isobutanol, hexanol, 2-ethylhexanol, and benzyl alcohol, secondary alcohols such as isopropanol, sec-butanol, cyclopentanol, cyclohexanol, and cycloheptanol, tertiary alcohols such as tert-butanol, and unsaturated alcohols such as allyl alcohol may be cited.

The amount of the alcohol to be used is not less than 5 moles, preferably in the range of from 6 to 25 moles, per mole of the maleinamic acid being used as the starting material. If the amount of the alcohol to be used is less than 5 moles, the maleinamic acid as the raw material will not be easily solved in the reaction solution and the corresponding maleinamic ester will be obtained only in a low yield with low selectivity because of such adverse consequences as an increase in the duration of the reaction of esterification, an increase in the amounts of by-products suffered to occur, and a stop of the reaction of esterification. Conversely, if the amount exceeds 25 moles, the reaction will suffer from poor productivity and will prove economically disadvantageous.

As typical examples of the maleinamic ester represented by the general formula (3) to be produced by the present invention, maleinamic methyl esters, maleinamic ethyl esters, maleinamic n-propyl esters, maleinamic isopropyl esters, maleinamic n-butyl esters, malainamic isobutyl esters, maleinamic sec-butyl esters, maleinamic tert-butyl esters, maleinamic hexyl esters, maleinamic cyclohexyl esters, N-methyl maleinamic methyl esters, N-methyl maleinamic ethyl esters, N-methyl maleinamic n-butyl esters, N-methyl maleinamic iso-butyl esters, N-methyl maleinamic 2-ethyl-hexyl esters, N-methyl maleinamic cyclohexyl esters, N-ethyl maleinamic methyl esters, N-ethyl maleinamic ethyl esters, N-ethyl maleinamic n-butyl esters, N-ethyl maleinamic iso-butyl esters, N-ethyl maleinamic 2-ethylhexyl esters, N-ethyl maleinamic cyclohexyl esters, N-n-propyl maleinamic methyl esters, N-n-propyl maleinamic ethyl esters, N-n-propyl maleinamic n-butyl esters, N-n-propyl maleinamic iso-butyl esters, N-n-propyl maleinamic 2-ethylhexyl esters, N-n-propyl maleinamic cyclohexyl esters, N-isopropyl maleinamic methyl esters, N-n-butyl maleinamic methyl esters, N-n-butyl maleinamic ethyl esters, N-n-butyl maleinamic n-butyl esters, N-n-butyl maleinamic iso-butyl esters, N-n-butyl maleinamic 2-ethylhexyl esters, N-n-butyl maleinamic cyclohexyl esters, N-sec-butyl maleinamic methyl esters, N-sec-butyl maleinamic ethyl esters, N-sec-butyl maleinamic n-butyl esters, N-sec-butyl maleinamic iso-butyl esters, N-sec-butyl maleinamic 2-ethylhexyl esters, N-sec-butyl maleinamic cyclohexyl esters, N-isobutyl maleinamic methyl esters, N-isobutyl maleinamic ethyl esters, N-isobutyl maleinamic n-butyl esters, N-isobutyl maleinamic iso-butyl esters, N-isobutyl maleinamic 2-ethylhexyl esters, N-isobutyl maleinamic cyclohexyl esters, N-tert-butyl maleinamic methyl esters, N-tert-butyl maleinamic ethyl esters, N-tert-butyl maleinamic n-butyl esters, N-tert-butyl maleinamic iso-butyl esters, N-tert-butyl maleinamic 2-ethylhexyl esters, N-tert-butyl maleinamic cyclohexyl esters, N-n-hexyl maleinamic methyl esters, N-n-hexyl maleinamic ethyl esters, N-n-hexyl maleinamic n-butyl esters, N-n-hexyl maleinamic iso-butyl esters, N-n-hexyl maleinamic 2-ethylhexyl esters, N-n-hexyl maleinamic cyclohexyl esters, N-octyl maleinamic methyl esters, N-octyl maleinamic ethyl esters, N-octyl maleinamic n-butyl esters, N-octyl maleinamic iso-butyl esters, N-octyl maleinamic 2 -ethyl-hexyl esters, N-octyl maleinamic cyclohexyl esters, N-decyl maleinamic methyl esters, N-decyl maleinamic ethyl esters, N-decyl maleinamic n-butyl esters, N-decyl maleinamic iso-butyl esters, N-decyl maleinamic 2-ethylhexyl esters, N-decyl maleinamic cyclohexyl esters, N-dodecyl maleinamic methyl esters, N-dodecyl maleinamic ethyl esters, N-dodecyl maleinamic n-butyl esters, N-dodecyl maleinamic iso-butyl esters, N-dodecyl maleinamic 2-ethylhexyl esters, N-dodecyl maleinamic cyclohexyl esters, N-octadecyl maleinamic methyl esters, N-octadecyl maleinamic ethyl esters, N-octadecyl maleinamic n-butyl esters, N-octadecyl maleinamic iso-butyl esters, N-octadecyl maleinamic 2-ethylhexyl esters, and N-octadecyl maleinamic cyclohexyl esters may be cited.

The catalyst which is contemplated by this invention is a sulfonic acid type catalyst, a mixture or salt of a maleinamic acid represented by the general formula (3) with sulfuric acid (hereinafter referred to briefly as "mixture"), or a mono(cyclo)alkyl sulfuric ester represented by the general formula (5):

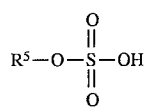

$$R^5-O-\overset{\overset{O}{\|}}{\underset{\underset{O}{\|}}{S}}-OH \qquad (5)$$

wherein $R^5$ is a cycloalkyl group of 1 to 8, preferably 3 to 8, carbon atoms.

The sulfonic acid type catalysts which are generally usable for the catalysis contemplated by this invention include sulfuric acid, sulfuric anhydride, aryl sulfonic acids such as p-toluene sulfonic acid and benzene sulfonic acid, alkyl sulfonic acids such as methyl sulfonic acid, ethyl sulfonic acid, propyl sulfonic acid, butyl sulfonic acid, and octyl sulfonic acid, and acidic ion-exchange resins, for example. Sulfuric acid proves particularly desirable among other catalysts mentioned above. One member or a mixture of two or more members selected from the group of sulfonic acid type catalysts cited above may be used.

It is suspected that when the catalyst is in the form of a mixture such as with sulfuric acid, for example, the sulfuric acid amide can be controlled to a suitable pH level and the sulfuric acid and the maleinamic acid can react with each other and, as a consequence, the mixture, besides fulfilling the intrinsic function as a mixture, partly or wholly goes the length of forming a compound like a salt and further exalting the activity of sulfuric acid as compared with the catalyst which is formed solely of sulfuric acid.

As typical examples of the mixture of the acid catalyst with a maleinamic acid to be used in this invention, the mixture of a maleinamic acid with sulfuric acid, the mixture of an N-methyl maleinamic acid with sulfuric acid, the mixture of an N-ethyl maleinamic acid with sulfuric acid, the mixture of an N-n-propyl maleinamic acid with sulfuric acid, the mixture of an N-isopropyl maleinamic acid with sulfuric acid, the mixture of an N-n-butyl maleinamic acid with sulfuric acid, the mixture of an N-isobutyl maleinamic acid with sulfuric acid, the mixture of an N-tert-butyl maleinamic acid with sulfuric acid, the mixture of an N-n-hexyl maleinamic acid with sulfuric acid, the mixture of an N-octyl maleinamic acid with sulfuric acid, the mixture of an N-decyl maleinamic acid with sulfuric acid, the mixture of an N-dodecyl maleinamic acid with sulfuric acid, the mixture of an N-octadecyl maleinamic acid with sulfuric acid, and the mixtures of the various maleinamic acids mentioned above with sulfuric anhydride, aryl sulfonic acids such as p-toluene sulfonic acid and benzene sulfonic acid, or alkyl sulfonic acids such as methyl sulfonic acid, ethyl sulfonic acid, and butyl sulfonic acid may be cited. The mono(cyclo)alkyl sulfuric esters which are effectively usable in this invention include monomethyl sulfuric esters, monoethyl sulfuric esters, monopropyl sulfuric esters, monobutyl sulfuric esters, monoisobutyl sulfuric esters, monohexyl sulfuric esters, monocyclopentyl sulfuric esters, monocyclohexyl sulfuric esters, monocycloheptyl sulfuric esters, monooctyl sulfuric esters, and mono(2-ethylhexyl) sulfuric esters, for example.

The amount of the catalyst to be used is preferably in the range of from 0.01 to 2 moles, preferably from 0.1 to 1 mole, per mole of the starting material. If the amount of the catalyst to be used is less than 0.01 mole, the reaction of esterification will consume an unduly long time or the esterification itself will fail to proceed. Conversely, if this amount exceeds 2 moles, the excess will do no good economically and will result in increasing the amount of by-products.

The inert solvent is a solvent which is inert to the raw-material maleinamic acid. As typical examples of the inert solvent, diethylene glycol methyl ether, ethylene glycol dimethyl ether, acetone, methylethyl ketone, diethyl ether, dioxane, tetrahydrofuran, sulforan, dimethyl sulfonoxide, dichloromethane, chloroform, benzene, toluene, xylene, pentane, hexane, cyclopentane, and cyclohexane may be cited. Preferably this inert solvent ought to avoid manifesting any activity to the raw-material maleinamic acid and form an azeotropic mixture with an alcohol. The inert solvents which answer this description include aliphatic hydrocarbons such as pentane, hexane, and cyclohexane and aromatic hydrocarbons such as benzene, toluene, and xylene.

As respects the amount of the inert catalyst to be used, it is preferable from the standpoint of enabling the reaction of esterification to proceed smoothly and, at the same time, satisfying the economic conditions, to use the inert catalyst in an amount in the range of from 0.1 to 20 moles, preferably from 0.5 to 15 moles, per mole of the alcohol. If the amount of the inert solvent to be used is unduly small, the expulsion of the formed water by distillation from the reaction system will be attained only with difficulty and the amount of by-products will increase. Conversely, if this amount is unduly large, the passage of the maleinamic acid into the reaction solution will be impeded and, as a consequence, the yield of the corresponding maleinamic ester will be lowered. Preferably, the amount of the inert solvent is not less than 0.1 mole, preferably in the range of from 0.3 to 16 moles, per mole of the maleinamic acid as the starting material.

The present reaction entails secondary reactions when the temperature thereof is unduly high, whereas it fails to proceed when the temperature is unduly low. The reaction temperature, therefore, is in the range of from 0° to 150° C., preferably from 10° to 100° C., and more preferably from 20° to 70° C. The reaction may proceed under normal pressure, an increased pressure, or a reduced pressure so long as the temperature of reaction falls in the range specified above. The reaction time is properly in the range of from 1 to 20 hours, preferably from 2 to 7 hours.

As regards the addition of the maleinamic ester, the alcohol, the inert organic solvent, and particularly the azeotropic solvent and the sulfonic acid type catalyst to the reaction system in the method of this invention, the order of their addition is not particularly critical. Since ideal stirring of the reaction system is indispensable for smooth progress of the reaction, it is preferable to add first the inert solvent, then the sulfonic acid type catalyst, and thereafter the alcohol and the maleinamic acid. The maleinamic acid may be added continuously, batchwise, or semi-batchwise. In a particularly preferable mode of embodiment of this invention, the kind of organic solvent is so selected that the azeotropic solvent used in the reaction may be identical with the organic solvent which has been specifically used in the production of the maleinamic acid as the raw material.

The maleinamic ester represented by the general formula (6) which is produced as described above is a polymerable monomer containing a double bond in the molecular unit thereof and can be radically homopolymerized or copolymerized to give rise to a heat-resistant thermoplastic resin.

As described above, the method of this invention produces a maleinamic ester represented by the general formula (6) in the presence of a sulfonic acid type catalyst easily in a high yield with high selectivity from a maleinamic acid represented by the formula (3) as the starting material.

It has been ascertained by our study that when ammonia gas is passed through a maleic anhydride solution, the reaction of maleic anhydride with ammonia proceeds at a notably high speed, that the formed maleinamic acid suddenly separates from the reaction solution because it is sparingly soluble in virtually all ordinary inert organic solvents, that this phenomenon occurs particularly conspicuously in the neighborhood of an orifice ejecting the ammonia gas into the reaction solution, and that, as a consequence, the crystals which have separated in the neighborhood of the orifice having a high gas concentration aggregate into lumps and inevitably block the orifice.

As a result, the passage of the ammonia gas into the maleic anhydride solution is impeded and the control of the supply of the ammonia gas is attained only with great difficulty and the production of a maleinamic acid of stable quality is not easily obtained. Moreover, since the unaltered maleic anhydride, ammonia, ammonium salt of maleinamic acid, etc. remain in large amounts in the reaction solution, the reaction solution must be refined by separation of the maleinamic acid therefrom so as to be efficiently used in the next cycle of esterification with alcohol. Since the blowing of ammonia gas into the maleic anhydride solution cannot be ideally controlled and the production of a maleinamic acid of high purity in a high yield cannot be attained as described above, the refinement of the reaction solution by the separation of the maleinamic acid therefrom has been an essential requirement for the production of maleinamic ester.

After studying the reaction of ammonia gas in the maleic anhydride solution, we have found that the blockage of the neighborhood of the orifice ejecting ammonia gas into the reaction solution with crystals of maleinamic acid can be precluded by curbing the sudden reaction of ammonia gas with the maleic anhydride and consequently the sudden separation of the formed maleinamic acid crystals, that the maleinamic acid of high purity can be consequently obtained in a high yield, and that the reaction solution can be subsequently used in its unaltered form, namely without being preparatorily refined by removal of the maleinamic acid therefrom, for the next cycle of esterification with an alcohol to permit efficient production of a maleinamic ester. We have perfected this invention based on this knowledge.

To be specific, this invention comprises firstly a method for the production of a maleinamic acid by the reaction of maleic anhydride with ammonia in an inert solvent, characterized in that the production is attained by placing a solution of the maleic anhydride in the inert solvent in a reactor, introducing meanwhile the ammonia gas into the empty space part of the reactor, allowing ammonia to be absorbed into the solution through the surface of contact between the solution and the ammonia gas, and inducing the reaction of the absorbed ammonia with the maleic anhydride.

It has been ascertained by our study that when ammonia gas is passed into a maleic anhydride solution, the reaction of the maleic anhydride with ammonia proceeds at a conspicuously high speed, that the formed maleinamic acid suddenly separates from the reaction solution because it has only sparing solubility in virtually all ordinary inert organic solvents, that this phenomenon occurs conspicuously in the neighborhood of an orifice ejecting the ammonia gas into the solution, and that consequently the crystals separated in the neighborhood of the orifice having a high gas concentration inevitably aggregate into lumps and block the orifice.

As a result, the passage of the ammonia gas into the maleic anhydride solution is impeded and the control of the supply of the ammonia gas is attained only with great difficulty and the production of a maleinamic acid of stable quality is not easily obtained. Besides, since the unaltered maleic anhydride, ammonia, ammonium salt of maleinamic acid, etc. remain in large amounts in the reaction solution, the reaction solution must be refined by removal of the maleinamic acid therefrom so as to be efficiently used in the next cycle of esterification with alcohol. Since the blowing of ammonia gas into the maleic anhydride solution cannot be ideally controlled and the production of a maleinamic acid of high purity in a high yield cannot be attained as described above, the refinement of the reaction solution by the separation of the maleinamic acid therefrom has been an essential requirement for the production of a maleinamic ester.

After studying the reaction of ammonia gas in the maleic anhydride solution, we have found that the blockage of the neighborhood of the orifice ejecting ammonia gas into the reaction solution with crystals of maleinamic acid can be precluded by curbing the sudden reaction of ammonia gas with the maleic anhydride and consequently the sudden separation of the formed maleinamic acid crystals, that the maleinamic acid of high purity can be consequently obtained in a high yield, and that the reaction solution can be subsequently used in its unaltered form, namely without being preparatorily refined by separation of the maleinamic acid therefrom, for the next cycle of esterification with an alcohol to permit efficient production of a maleinamic ester. We have perfected this invention on the basis of this knowledge.

To be specific, this invention comprises secondly a method for the production of a maleinamic acid by the reaction of maleic anhydride with ammonia in an inert solvent, characterized in that the production is attained by carrying out the reaction while supplying the maleic anhydride and ammonia to the reaction solution so that the concentration of the maleic anhydride in the reaction solution may be kept at a level of not more than 10% by weight.

After further studying methods for the production of maleinamic acid, we have found:

(a) that when ammonia is solved preparatorily in an inert solvent and a maleic anhydride solution is added dropwise into the ammonia solution, the reaction of the maleic anhydride with ammonia mainly proceeds near the surface of the solution on which the maleic anhydride solution impinges, (b) that the reaction near the surface of the solution mentioned above is continued by adjusting the supply of the maleic anhydride and ammonia to the reaction system so that the amount of ammonia may be always in excess of that of the maleic anhydride, namely an excess ammonia always remains in the reaction system, (c) that, in comparison with the conventional method which suffers the reaction of the maleic anhydride with ammonia gas to proceed suddenly in the neighborhood of the orifice ejecting ammonia gas as described above, the method mentioned above permits easy control of the amount of ammonia gas because the reaction proceeds mainly in the boundary of the ammonia solution on which the maleic anhydride solution being added dropwise thereto impinges and the orifice for ejection of ammonia is not blocked, (d) that the sudden separation of the formed maleinamic acid can be curbed because the reaction proceeds mainly in the boundary and the ammonia concentration is low near the boundary and, as a consequence, no unaltered ammonia is occluded any longer in the formed maleinamic acid and the maleinamic acid of high purity can be obtained in a high yield, and (e) that since the formed maleinamic acid has high purity, the maleinamic acid in the reaction solution can be subsequently used for the esterification with the alcohol compound to permit efficient production of a maleinamic ester without requiring the reaction solution to be refined by removal of the maleinamic acid therefrom in advance of the esterification. We have perfected this invention on the basis of this knowledge.

To be specific, this invention comprises thirdly a method for the production of a maleinamic acid by the reaction of maleic anhydride with ammonia in an inert solvent, characterized in that the production is attained by carrying out the reaction while keeping the ammonia concentration in the reaction solution at a level of not less than 0.01% by weight.

The production of a maleinamic acid from maleic anhydride can be efficiently attained by using each of the first to third steps for production of maleinamic acid mentioned above as a First Step and combining this First Step with a Second Step which comprises adding an alcohol to the maleinamic acid-containing reaction solution obtained in the First Step and heating the resultant mixture in the presence of an acid catalyst thereby esterifying the maleinamic acid and producing a corresponding maleinamic ester.

As the inert solvent for this invention, one member or a mixture of two or more members selected from among various organic solvents which are generally accepted as inert solvents can be used. As typical examples of the inert solvent, diethylene glycol dimethyl ether, ethylene glycol dimethyl ether, acetone, methylethyl ketone, diethyl ether, dioxane, tetrahydrofuran, sulforan, dimethyl sulfoxide, dimethyl formamide, dichloromethane, chloroform, benzene, toluene, xylene, pentane, hexane, cyclopentane, and cyclohexane may be cited.

As respects the amount of the inert solvent to be used, since the maleinamic acid is sparingly soluble in the organic solvent and the maleinamic acid formed by the reaction assumes the constitution of a slurry, it is preferable to use the inert solvent in an amount of not less than 1 part, preferably from 3 to 20 parts, based on 1 part of the maleic anhydride as the raw material in due consideration of the ease with which the reaction solution is stirred and transferred.

The first invention produces a maleinamic acid by placing a solution of maleic anhydride in the inert solvent in a reactor, meanwhile introducing into the empty space part of the reactor an equimolar amount or less of ammonia gas relative to the maleic anhydride, allowing ammonia to be solved into the solution through the surface of contact between the maleic anhydride solution and the ammonia gas, and enabling the solved ammonia to react with the maleic anhydride in the inert solvent.

The pressure (absolute pressure) of ammonia gas in the empty space part of the reactor is in the range of from 0.1 to 10 atmospheres, preferably from 1 to 2 atmospheres. Since the ammonia is consumed and the pressure thereof is decreased in proportion as the reaction proceeds, it is preferable to introduce an inert gas into the empty space part of the reactor from time to time so as to keep the pressure inside the empty space part in the range specified above. Nitrogen, argon, etc. can be used as the inert gas. As the reactor, a pressure reactor such as, for example, an autoclave is favorably used.

The maleic anhydride solution is preferably stirred for the purpose of promoting the absorption of ammonia by the solution. The reaction temperature is in the range of from 10° to 100° C., preferably from 20° C. to 60° C.

In this invention, after the reaction is completed, the reaction solution is preferable to be continuously stirred for the sake of aging at a temperature in the range of from 10° to 100° C., preferably from 50° to 80° C., for a period in the range of from 0.1 to 4 hours, preferably from 0.5 to 2 hours. Owing to the aging, the unaltered maleic anhydride and ammonia still remaining in the reaction system are made to interreact further and consequently the formed maleinamic acid is allowed to acquire a notably exalted purity.

In this invention, since the ammonia destined to react with the maleic anhydride is supplied through the surface of contact between the maleic anhydride solution and the ammonia gas, the otherwise possible sudden formation of maleinamic acid is curbed and the formed maleinamic acid is obtained in the form of minute crystals. Thus, the aggregation of maleinamic acid crystals into lumps and the consequent blockage of the orifice ejecting ammonia gas with the lumps and the defilement of minute maleinamic acid crystals with coarse lumps can be precluded, with the result that the maleinamic acid of high purity will be obtained in a high yield.

The first characteristic of the second invention resides in carrying out the reaction of the maleic anhydride with ammonia in the inert solvent while continuing the supply of the maleic anhydride and ammonia to the reaction solution. To be specific, the maleic anhydride normally solved in the same inert solvent as is used in the reaction solution or the maleic anhydride fused by heating is added to the inert solvent and, at the same time, ammonia, generally ammonia gas, of an equimolar amount or less relative to the maleic anhydride is supplied to the inert solvent and allowed to react therein with the maleic anhydride. Alternatively, part of the maleic anhydride as the raw material may be solved in the inert solvent in advance of the start of the reaction and the remaining maleic anhydride and ammonia may be supplied to the resultant maleic anhydride solution and allowed to interreact therein.

The second characteristic of the second invention resides in carrying out the reaction of the maleic anhydride with ammonia under the conditions such that the maleic anhydride concentration in the reaction solution may remain at a level of not more than 10% by weight. For the purpose of keeping the maleic anhydride concentration in the reaction solution at a level of not more than 10% by weight, it suffices to adjust suitably the rates of supply of the maleic anhydride and ammonia to the reaction solution or the concentration of the maleic anhydride solution to be supplied.

If the maleic anhydride concentration in the reaction solution exceeds 10% by weight, the object of this invention cannot be accomplished because of such drawbacks as the sudden formation of a maleinamic acid and the blockage of the neighborhood of the orifice ejecting ammonia gas with coarse lumps of maleinamic acid crystals. If the maleic anhydride concentration in the reaction solution is unduly low, the reaction consumes so much time as to render the operation of production economically impracticable. Thus, the maleic anhydride concentration is generally in the range of from 1 to 10% by weight, preferably from 2 to 6% by weight.

The supply of the maleic anhydride and ammonia to the reaction solution may be performed either continuously or intermittently. Generally for the purpose of curbing the sudden formation of a maleinamic acid, however, the supply is desired to be made continuously. Ammonia is generally blown into the reaction solution in the form of ammonia gas and, therefore, the contact of the maleic anhydride with ammonia is attained uniformly. When the reaction solution is stirred, however, the reaction yields still better results because the concentration distribution of the reactants in the reaction solution gains in uniformity.

The reaction temperature is generally in the range of from 10° to 100° C., preferably from 20° to 60° C.

In this invention, after the supply of the maleic anhydride and ammonia to the reaction solution has been completed, the reaction solution is preferable to be stirred for the sake of aging at a temperature in the range of from 10° to 100° C., preferably from 50° to 80° C. The stirring of the reaction solution is preferable to be continued for a period in the range of from 0.1 to 4 hours, preferably from 0.5 to 2 hours, at a temperature in the range specified above. By the aging, the purity of the formed maleinamic acid is notably increased because the unaltered maleic anhydride and ammonia still remaining in the reaction system are caused to interreact further.

In this invention, the sudden formation of a maleinamic acid is curbed and consequently the formed maleinamic acid is obtained in the form of minute crystals by carrying out the reaction while continuing the supply of the maleic anhydride and ammonia to the reaction solution in such a manner as to keep the maleic anhydride concentration in the reaction solution at a level of not more than 10% by weight. As a result, the aggregation of maleinamic acid crystals into lumps and the consequent blockage of the orifice ejecting ammonia gas with the lumps and the defilement of the maleinamic acid crystals with coarse lumps can be precluded. Thus, the maleinamic acid of high purity is stably obtained in a high yield.

The characteristic of the third invention resides in carrying out the reaction of the maleic anhydride with ammonia in the inert solvent under the condition of allowing excess ammonia to remain in the reaction solution, namely the condition of keeping the ammonia concentration in the reaction solution at a level of not less than 0.01% by weight. The reaction of this invention can be implemented by the following methods, for example. It should be understood, however, that this invention is not limited to these methods.

(a) A method which comprises simultaneously supplying ammonia and the maleic anhydride into the inert solvent and allowing them to react with each other therein.

(b) A method which comprises preparatorily solving ammonia in the inert solvent and subsequently supplying the maleic anhydride and ammonia into the resultant ammonia solution and allowing them to react with each other therein.

(c) A method which comprises solving ammonia in the inert solvent and subsequently supplying the maleic anhydride into the resultant solution thereby allowing the maleic anhydride to react with ammonia therein or repeating the procedure just mentioned.

No matter which of these methods may be employed, the ammonia concentration in the reaction solution must be always kept at a level of not less than 0.01% by weight from the start to the end of the reaction. The ammonia concentration is kept preferably in the range of from 0.03 to 0.5% by weight. If the ammonia concentration in the reaction solution is less than 0.01% by weight, then the reaction occurring mainly near the surface of the reaction solution as described above will not easily proceed and consequently the reaction time will be so elongated as to impair the productivity of the reaction. If the supply of ammonia surpasses the limit of solution of ammonia in the inert solvent, then the excess ammonia will pass in the form of vapor into the gaseous phase. Thus, the upper limit of the ammonia concentration in the reaction solution ought to be decided by the solubility of ammonia in the inert solvent. In other words, the ammonia concentration in the reaction solution may be suitably selected in the range of from 0.01% by weight to the solubility of ammonia in the inert solvent.

For the purpose of keeping the ammonia concentration in the reaction solution at a level of not less than 0.01% by weight, it suffices to adjust suitably the rates of supply of ammonia and the maleic anhydride and the concentration of the maleic anhydride solution to be supplied. Generally, the amount of ammonia to be supplied is in the approximate range of from 1 to 3 moles per mole of the maleic anhydride.

The supply of ammonia is generally accomplished by blowing ammonia gas into the reaction solution. In this case, the reaction yields highly desirable results because the introduced ammonia gas imparts increased uniformity to the concentration distribution of reactants in the reaction solution. The maleic anhydride may be supplied in the form of a solution thereof in the inert solvent or it may be supplied in a state fused by heating. When the maleic anhydride is solved in the inert solvent, the maleic anhydride concentration in the resultant solution may be suitably decided.

The supply of ammonia and the maleic anhydride to the reaction solution may be carried out either continuously or intermittently. Generally, for the sake of precluding the sudden formation of the maleinamic acid, this supply is preferable to be made continuously.

The reaction temperature is generally in the range of from 10° to 100° C., preferably from 20° to 60° C.

In this invention, after the supply of the maleic anhydride and ammonia to the reaction solution has been completed, the reaction solution is preferable to be stirred for the sake of aging at a temperature in the range of from 10° to 100° C., preferably from 50° to 80° C. The stirring of the reaction solution is preferable to be continued for a period in the range of from 0.1 to 4 hours, preferably from 0.5 to 2 hours, at a temperature in the range mentioned above. Owing to the aging, the purity of the formed maleinamic acid is notably increased because the unaltered maleic anhydride and ammonia still remaining in the reaction system are caused to react with each other further.

The maleinamic acid which is formed by the reaction of the maleic anhydride with ammonia exists in the form of a slurry in the reaction solution. The separation of the maleinamic acid from the reaction solution can be implemented by various methods heretofore known to the art. The maleinamic acid which has been so separated may be mixed anew with an alcohol and esterified into a corresponding maleinamic ester.

In this invention, the maleinamic acid is obtained with high purity in a high yield by the reaction of the maleic anhydride with ammonia. The reaction solution obtained in this case, therefore, can be directly combined with an alcohol and heated in the presence of an acid catalyst so as to be esterified into a maleinamic ester unlike the reaction solution obtained by the conventional method which is required to be refined by the separation of the formed maleinamic acid therefrom in advance of the esterification.

The conditions of esterification contemplated by the present invention are as described above. The alcohol to be used for the esterification can be any of the alcohols which are represented by the general formula (4) mentioned above. In the case of an alcohol incorporating a phenyl group or a benzyl group, it may further contain within the group such a substituent group as a lower alkyl group or a halogen atom. Phenol, cresol, benzyl alcohol, etc. may be cited as typical examples.

The amount of the alcohol to be used is in the range of from 1 to 30 moles, preferably from 2 to 15 moles, per mole of the maleinamic acid. The method for the addition of the alcohol is not particularly critical. The alcohol may be continuously or intermittently added proportionately to the progress of the reaction. Otherwise, it may be added collectively.

As the acid catalyst for use in the esterification of this invention, any of the well-known acid catalysts which are generally accepted for use in reactions of esterification can be used. For example, inorganic acids such as sulfuric acid, hydrochloric acid, nitric acid, carbonic acid, and phosphoric acid, composites having such inorganic acids deposited on such inorganic carriers as silica, organic acids such as p-toluene sulfonic acid, methane sulfonic acid, benzene sulfonic acid, ethyl sulfonic acid, and octyl sulfonic acid, and acidic ion-exchange resins can be used. The timing for the addition of the acid catalyst is not particularly critical. The acid catalyst may be added to the reaction system prior to the production of a maleinamic acid or prior to the esterification of the maleinamic acid with an alcohol.

The amount of the acid catalyst to be used is variable with the kind of catalyst to be used and, therefore, cannot be uniquely specified. Generally, the acid catalyst is preferable to be used in an amount in the range of from 0.0001 to 30 parts, preferably from 0.001 to 10 parts, based on 1 part of the maleic anhydride being used as the raw material.

The esterification of this invention is advantageously carried out at a temperature in the range of from 20° to 180° C., preferably from 70° to 130° C. The reaction pressure is not particularly critical. The esterification may be performed under normal pressure, a reduced pressure, or an increased pressure, whichever suits the occasion.

The water formed in consequence of the esterification of this invention may be, or may not be, expelled in conjunction with the inert solvent by distillation from the reaction system.

Now, this invention will be described more specifically below with reference to working examples. It should be clearly understood that this invention is not limited by these examples.

EXAMPLE 1

In a flask having an inner volume of 500 ml and provided with a thermometer, a condenser, and a stirrer, 10.0 g (58.4 millimoles) of maleinamic n-butyl ester, 1.6 g (10.4 millimoles) of mono-n-butyl sulfuric ester, 40.0 g of toluene, and 0.01 g of copper dibutyl dithiocarbamate were placed and left reacting therein under a refluxing condition. The reaction was completed after 2 hours' stirring. When the reaction solution was filtered and the solution separated by the filtration was assayed by nuclear magnetic resonance, it was identified to be a maleinimide with a purity of 93 mole %. The assay of the solution by gas chromatography revealed that the maleinimide was obtained in a yield of 68.0 mole % based on the maleinamic n-butyl ester. The results are shown in Table 1.

EXAMPLES 2 AND 3

Maleinimides were obtained in yields shown in Table 1 by following the procedure of Example 1 while using maleinamic n-butyl ester as the raw material and mono-n-butyl sulfuric ester as the catalyst and changing the amount of catalyst as shown in Table 1.

EXAMPLES 4 TO 6

Maleinimides were obtained in yields shown in Table by following the procedure of Example 1 while using maleinamic 2-ethylhexyl ester as the raw material and mono-2-ethylhexyl sulfuric ester as the catalyst and changing the amount of catalyst as shown in Table 1.

TABLE 1

| Example | Amount of catalyst/raw material (molar ratio) | Yield (in mole % based on raw material) |
|---|---|---|
| 1 | 0.18 | 68.0 |
| 2 | 0.06 | 62.3 |
| 3 | 0.70 | 70.9 |
| 4 | 0.18 | 65.1 |
| 5 | 0.06 | 63.4 |
| 6 | 0.70 | 70.9 |

EXAMPLE 7

In a flask having an inner volume of 500 ml and provided with a thermometer, a condenser, and a stirrer, 10.0 g (58.4 millimoles) of maleinamic n-butyl ester, 1.6 g (10.4 millimoles) of mono-n-butyl sulfuric ester, 40.0 g of xylene, and 0.01 g of copper dibutyl dithiocarbamate were placed and left reacting therein under a refluxing condition. The reaction was completed after 2 hours' stirring. When the reaction solution was filtered and the solution separated by the filtration was assayed by nuclear magnetic resonance, it was identified to be a maleinimide with a purity of 89 mole %. The assay of the solution by gas chromatography revealed that the maleinimide was obtained in a yield of 78 mole % based on the maleinamic n-butyl ester. The results are shown in Table 2.

EXAMPLES 8 TO 10

Maleinimides were obtained in yields shown in Table 2 by following the procedure of Example 7 while using maleinamic ethyl ester as the raw material and monoethyl sulfuric ester as the catalyst and changing the amount of the catalyst as shown in Table 2.

EXAMPLES 11 TO 13

Maleinimides were obtained in yields shown in Table 2 by following the procedure of Example 7 while using maleinamic cyclohexyl ester as the raw material and monocyclohexyl sulfuric ester as the catalyst and changing the amount of the catalyst as shown in Table 2.

TABLE 2

| Example | Amount of catalyst/raw material (molar ratio) | Yield (in mole % based on raw material) |
|---|---|---|
| 7 |  | 78.0 |
| 8 | 0.18 | 86.3 |
| 9 | 0.06 | 73.2 |
| 10 | 0.70 | 90.9 |
| 11 | 0.18 | 70.3 |
| 12 | 0.06 | 68.6 |
| 13 | 0.70 | 78.8 |

EXAMPLE 14

In a flask having an inner volume of 500 ml and provided with a thermometer, a condenser furnished with a water separator, and a stirrer, 10.0 g (58.4 millimoles) of maleinamic n-butyl ester, 1.6 g (10.4 millimoles) of mono-n-butyl sulfuric ester, 40.0 g of toluene, and 0.01 g of copper dibutyl dithiocarbamate were placed and left reacting therein at a temperature of 115° C. The n-butyl alcohol formed by the reaction was expelled by distillation from the reaction system. The reaction was completed after one hours' stirring. When the reaction solution was filtered and the solution separated by the filtration was assayed by nuclear magnetic resonance, it was identified to be a maleinimide with a purity of 99 mole %. The assay of the solution by gas chromatography revealed that the maleinimide was obtained in a yield of 90 mole % based on the maleinamic n-butyl ester. The results are shown in Table 3.

EXAMPLE 15

In a flask having an inner volume of 500 ml and provided with a thermometer, a condenser furnished with a water separator, and a stirrer, 10.0 g (58.4 millimoles) of maleinamic n-butyl ester, 1.6 g (10.4 millimoles) of mono-n-butyl sulfuric ester, 40.0 g of xylene, and 0.01 g of copper dibutyl dithiocarbamate were placed and left reacting therein at a temperature of 145° C. The n-butyl alcohol formed by the reaction was expelled by distillation from the reaction system. The reaction was completed after one hour's stirring. When the reaction solution was filtered and the solution separated by the filtration was assayed by nuclear magnetic resonance, it was identified to be a maleinimide with a purity of 99 mole %. The assay of the solution by gas chromatography revealed that the maleinimide was obtained in a yield of 95 mole % based on the maleinamic n-butyl ester. The results are shown in Table 3.

EXAMPLE 16 AND 17

Maleinimides were obtained in yields shown in Table 3 by following the procedure of Example 15 while using maleinamic n-butyl ester as the raw material and mono-n-butyl sulfuric ester as the catalyst and changing the amount of the catalyst as shown in Table 3.

EXAMPLES 18 TO 20

Maleinimides were obtained in yields shown in Table 3 by following the procedure of Example 15 while using maleinamic 2-ethylhexyl ester as the raw material and mono-2-ethylhexyl sulfuric ester as the catalyst and changing the amount of the catalyst as shown in Table 3.

TABLE 3

| Example | Amount of catalyst/raw material (molar ratio) | Yield (in mole % based on raw material) |
|---|---|---|
| 14 |  | 90.0 |
| 15 | 0.18 | 95.0 |
| 16 | 0.06 | 90.3 |
| 17 | 0.70 | 97.1 |
| 18 | 0.18 | 90.2 |
| 19 | 0.06 | 87.5 |
| 20 | 0.70 | 92.3 |

EXAMPLE 21

In a flask having an inner volume of 500 ml and provided with a thermometer, a condenser furnished with a water separator, and a stirrer, 10.0 g (58.4 millimoles) of maleinamic n-butyl ester, 0.8 g (5.2 millimoles) of mono-n-butyl sulfuric ester, 0.3 g (2.94 millimoles) of sulfuric acid, 40.0 g of xylene, and 0.01 g of copper dibutyl dithiocarbamate were placed and left reacting therein at a temperature of 145° C. The n-butyl alcohol formed by the reaction was expelled by distillation from the reaction system. The reaction was completed after one hour's stirring. When the reaction solution was filtered and the solution separated by the filtration was assayed by nuclear magnetic resonance, it was identified to be a maleinimide with a purity of 97 mole %. The assay of the solution by gas chromatography revealed that the maleinimide was obtained in a yield of 91 mole % based on the maleinamic n-butyl ester.

CONTROL 1

In a four-neck flask having an inner volume of 500 ml and provided with a thermometer, a condenser furnished with a water separator, a toluene supply tube, and a stirrer, 23.0 g (0.2 mole) of maleinamic acid, 180 ml of toluene, 55.3 g (0.6 mole) of isobutyl alcohol, and 2.0 ml of concentrated sulfuric acid were placed and left reacting as heated and stirred at a temperature of 80° C. under a reduced pressure while the water formed by the reaction was expelled meanwhile together with toluene by distillation from the system. The esterification thus induced was continued for one hour. In this case, the reaction solution was in the form of a slurry. Then, the reaction solution in the flask was relieved of the reduced pressure and 0.1 g of p-methoxy phenol was added to the reaction solution still kept at 80° C. The reaction solution still under normal pressure was set heating. At the time that toluene began refluxing, toluene was supplied through the toluene supply tube at a flow rate of 180 ml/hr into the flask and, at the same time, the reaction solvent was extracted at a flow rate of 180 ml/hr through the water separator. The ensuing reaction was continued with the reaction solution kept stirred for 3 hours. At this time, the reaction system was in the form of a slurry partly containing solid lumps. After the reaction was completed, the reaction solution was filtered. When the solid lumps separated by the filtration were assayed by high-speed liquid chromatography, they were found to contain 3.2 mole % of a maleinimide. When the organic layer remaining after the filtration was assayed by gas chromatography, it was found to contain 6.0 mole % of the maleinimide. The results indicate that the maleinimide was obtained in a total yield of only 9.2 mole % based on the maleinamic acid used as the raw material.

CONTROL 2

In a three-neck flask having an inner volume of 200 ml and provided with a thermometer, a condenser furnished with a water separator, and a stirrer, 17.2 g (0.1 mole) of maleinamic n-butyl ester, 90 ml of toluene, 74.0 g (1.0 mole) of n-butyl alcohol, and 1.0 ml of concentrated sulfuric acid were placed and left reacting as heated and stirred under a refluxing condition for 3 hours. When the reaction solution obtained at the end of the reaction was assayed by high-speed liquid chromatography, it was found to have produced a maleinimide in a yield of 51.3 mole % based on the maleinamic n-butyl ester used as the raw material.

CONTROL 3

In a three-neck flask having an inner volume of 200 ml and provided with a thermometer, a condenser furnished with a water separator, and a stirrer, 12.9 g (0.1 mole) of maleinamic methyl ester, 90 ml of toluene, 32.0 g (1.0 mole) of methyl alcohol, and 1.0 ml of concentrated sulfuric acid were placed and left reacting as heated and stirred under a refluxing condition for 3 hours. When the reaction solution obtained at the end of the reaction was assayed by high-speed liquid chromatography, it was found to have produced a maleinimide in a yield of 10.0 mole % based on the maleinamic methyl ester used as the raw material.

CONTROL 4

In a three-neck flask having an inner volume of 200 ml and provided with a thermometer, a condenser furnished with a water separator, and a stirrer, 17.2 g (0.1 mole) of maleinamic n-butyl ester, 90 ml of n-butyl alcohol, and 0.8 g of sodium carbonate were placed and left reacting at room temperature (25° C.) as kept stirred for 3 hours. After the reaction was completed, the catalyst was removed from the reaction solution by filtration. When the reaction solution was assayed by high-speed liquid chromatography, it was found to have produced a maleinimide in a yield of 27.9 mole % based on the maleinamic n-butyl ester used as the raw material.

EXAMPLE 22

In a flask having an inner volume of 500 ml and provided with a thermometer, a condenser furnished with a water separator, and a stirrer, 12.9 g (0.1 mole) of maleinamic methyl ester, 103.2 g of toluene, and 0.01 g of copper dibutyl dithiocarbamate were placed and, in the presence of 2.0 g of a catalyst having orthophosphoric acid deposited (in a concentration of 33% by weight) on a silica carrier having an average particle diameter of 150 m (produced by Fuji-Davison K.K. and marketed under trademark designation of "Microbead Silica 4B"), heated and stirred at 100° C. for 3 hours to effect a reaction for removal of alcohol. In this while, the alcohol which was formed by the reaction and evaporated from the reaction solution was expelled by distillation from the system. The reaction solution obtained at the end of the reaction was found to have an alcohol content of 0.3% by weight. The reaction solution was filtered to separate the catalyst. When the filtrate was assayed by gas chromatography, the maleinimide was found to account for a yield of 55.0 mole % based on the maleinamic methyl ester used as the raw material.

EXAMPLES 23 TO 25

Maleinamic methyl esters were subjected to the treatment for removal of alcohol by following the procedure of Example 22 while changing the reaction temperature, the amount of the catalyst, and the kind of catalyst as shown in Table 4. The results are shown in Table 4.

TABLE 4

| Example | Reaction temperature (°C.) | Amount of catalyst (g) | Organic solvent | Alcohol conc. in system (wt %) | Yield of maleinimide (mole %) |
| --- | --- | --- | --- | --- | --- |
| 23 | 100 | 4.0 | toluene | 0.3 | 63.5 |
| 24 | 130 | 2.0 | xylene | 0.1 | 73.8 |
| 25 | 130 | 4.0 | xylene | 0.1 | 88.2 |

Alcohol conc. in system: Alcohol concentration in the reaction solution at the end of the reaction.

EXAMPLE 26

In a flask having an inner volume of 500 ml and provided with a thermometer, a condenser furnished with a water separator, and a stirrer, 12.9 g (0.1 mole) of maleinamic methyl ester, 103.2 g of toluene, and 0.01 g of copper dibutyl dithiocarbamate were placed and, in the presence of 2.0 g of a catalyst having concentrated sulfuric acid deposited (in a concentration of 33% by weight) on the same silica carrier as used in Example 22, heated and stirred at 100° C. for 3 hours to effect a reaction for removal of alcohol. In this while, the alcohol which was formed by the reaction and evaporated from the reaction solution was expelled by distillation from the system. The reaction solution obtained at the end of the reaction was found to have an alcohol content of 0.3% by weight. The reaction solution was filtered to separate the catalyst. When the filtrate was assayed by gas chromatography, the maleinimide was found to account for a yield of 48.0 mole % based on the maleinamic methyl ester used as the raw material.

CONTROL 5

A maleinimide was produced from a maleinamic acid by following the procedure disclosed in JP-A-03-184,956 for the production of an N-substituted maleinimide from a corresponding N-substituted maleinamic acid, with necessary modifications.

In a four-neck flask having an inner volume of 500 ml and provided with a thermometer, a condenser furnished with a water separator, a toluene supply tube, and a stirrer, 23.0 g (0.2 mole) of a maleinamic acid, 180 ml of toluene, 55.3 g (0.6 mole) of isobutyl alcohol, and 2.0 ml of concentrated sulfuric acid were placed and left reacting as heated and stirred at a temperature of 80° C. under a reduced pressure while the water formed by the reaction was expelled meanwhile together with toluene by distillation from the system. The ensuing reaction of esterification was continued for one hour. Then, the reaction solution in the flask was relieved of the reduced pressure and 0.1 g of p-methoxyphenol was added to the reaction solution still kept at 80° C. The reaction solution still under normal pressure was set heating. At the time that toluene began refluxing, toluene was supplied through the toluene supply tube at a flow rate of 180 ml/hr i into the flask and, at the same time, toluene was extracted at a flow rate of 180 ml/hr through the water separator. At this time, the reaction system was in the state of a slurry partly containing solid lumps. After the reaction was completed, the reaction solution was filtered. When the solid lumps separated by the filtration were assayed by high-speed liquid chromatography, they were found to contain 3.2 mole % of a maleinimide. When the organic layer remaining after the filtration was assayed by gas chromatography, it was found to contain 6.0 mole % of the maleinimide. The results indicate that the maleinimide was obtained in a total yield of only 9.2 mole % based on the maleinamic acid used as the raw material.

CONTROL 6

A maleinimide was produced from a maleinamic ester by following the procedure disclosed in JP-A-03-173,866 for the production of an N-substituted maleinimide from a corresponding N-substituted maleinamic ester, with necessary modifications.

In a three-neck flask having an inner volume of 200 ml and provided with a thermometer, a condenser furnished with a water separator, and a stirrer, 12.9 g (0.1 mole) of maleinamic methyl ester, 90 ml of toluene, 32.0 g (1.0 mole) of methyl alcohol, and 1.0 ml of concentrated sulfuric acid were placed and left reacting as heated and stirred under a refluxing condition for removal of alcohol for 3 hours. The reaction solution obtained at the end of the reaction was assayed by high-speed liquid chromatography to determine the amount of a maleinimide produced. The results indicate that the maleinimide was obtained in a yield of only 10.0 mole % based on the maleinamic methyl ester used as the raw material.

CONTROL 7

A maleinimide was produced from a maleinamic ester by following the procedure disclosed in JP-A-04-221,365 for the production of an N-substituted maleinimide from a corresponding N-substituted maleinamic ester, with necessary modifications.

In a three-neck flask having an inner volume of 200 ml and provided with a thermometer, a condenser furnished with a water separator, and a stirrer, 12.9 g (0.1 mole) of maleinamic methyl ester, 90 ml of methyl alcohol, and 0.8 g of sodium carbonate were placed and left reacting as stirred at room temperature (25° C.) for removal of alcohol for 3 hours. After the reaction was completed, the reaction solution was filtered to remove the catalyst. Then, the reaction solution was assayed by high-speed liquid chromatography to determine the amount of a maleinimide produced. The results indicate that the maleinimide was obtained at a yield of only 27.9 mole % based on the maleinamic methyl ester used as the raw material.

EXAMPLE 27

In a reduced-pressure distillation apparatus provided with a flask 500 ml in inner volume, 129.0 g (1.0 mole) of maleinamic methyl ester and 0.1 g of copper dibutyl dithiocarbamate were placed and left reacting for removal of alcohol at a reaction temperature of 150° C. under an operating pressure of 15 mmHg. The distillate was introduced into a receptacle and collected therein, to obtain 64.2 g of a white solid substance.

When this white solid substance was assayed by nuclear magnetic resonance, it was identified to be a maleinimide. When the white solid substance was assayed by gas chromatography, it was found to have a maleinimide content of not less than 99.5 mole %. The results, therefore, indicate that the maleinimide was obtained in a yield of 65.9 mole % based on the maleinamic methyl ester used as the raw material.

EXAMPLES 28 TO 31

The reaction of maleinamic methyl ester for removal of alcohol was carried out by following the procedure of Example 27 while changing the reaction temperature, the operating pressure, and the use of catalyst as shown in Table 5. The results are shown in Table 5.

TABLE 5

| Example | Reaction temperature (°C.) | Operating pressure (mmHg) | Catalyst | Yield (mole %) |
|---|---|---|---|---|
| 28 | 160 | 24 | None | 68.3 |
| 29 | 150 | 15 | Acidic ion-exchange resin (1) | 72.7 |
| 30 | 150 | 15 | Silica-carried phosphoric acid (2) | 96.5 |
| 31 | 130 | 8 | Silica-carried phosphoric acid (2) | 70.8 |

(1) Strongly acidic ion-exchange resin (produced by Mitsubishi Chemical Co., Ltd. and marketed under trademark designation of "DIAION-PK216"); amount used 7.2 g.
(2) Orthophosphoric acid carried in a concentration of 33% on a silica carrier having a particle diameter of 150 m (produced by Fuji-Davison K.K.); amount used 2.0 g.

CONTROL 8

A maleinimide was produced from maleinamic acid by following the procedure disclosed in JP-A-03-184,956 for the production of an N-substituted maleinimide from a corresponding N-substituted maleinamic acid, with necessary modifications.

In a four-neck flask having an inner volume of 500 ml and provided with a thermometer, a condenser furnished with a water separator, a toluene supply tube, and a stirrer, 23.0 g (0.2 mole) of maleinamic acid, 180 ml of toluene, 55.3 g (0.6 mole) of isobutyl alcohol, and 2.0 ml of concentrated sulfuric acid were placed and left reacting as heated and stirred at a temperature of 80° C. under a reduced pressure while the water formed by the reaction was expelled together with toluene by distillation from the system. The esterification was continued for one hour. At this time, the reaction solution was in the form of a slurry. Then, the reaction solution in the flask was relieved of the reduced pressure and 0.1 g of p-methoxyphenol was added to the reaction solution still kept at 80° C. The reaction solution still under normal pressure was set heating. At the time that toluene began refluxing, toluene was supplied through the toluene supply tube at a flow rate of 180 ml/hr into the flask and, at the same time, toluene was extracted at a flow rate of 180 ml/hr through the water separator. At this time, the reaction system was in the form of a slurry partly containing solid lumps. After the reaction was completed, the reaction solution was filtered. When the solid lumps separated by the filtration were assayed by high-speed liquid chromatography, they were found to contain 3.2 mole % of a maleinimide. When the organic layer remaining after the filtration was assayed by gas chromatography, it was found to contain 6.0 mole % of the maleinimide. The results indicate that the maleinimide was obtained in a total yield of only 9.2 mole % based on the maleinamic acid used as the raw material.

CONTROL 9

A maleinimide was produced from a maleinamic ester by following the procedure disclosed in JP-A-02-173,866 for the production of an N-substituted maleinimide from a corresponding N-substituted maleinamic monoester.

In a three-neck flask having an inner volume of 200 ml and provided with a thermometer, a condenser furnished with a water separator, and a stirrer, 12.9 g (0.1 mole) of maleinamic methyl ester, 90 ml of toluene, 32.0 g (1.0 mole) of methyl alcohol, and 1.0 ml of concentrated sulfuric acid were placed and left reacting for removal of alcohol as heated and stirred under a refluxing condition for 3 hours. The reaction solution obtained at the end of the reaction was assayed by high-speed liquid chromatography to determine the amount of a maleinimide produced. The results indicate that the maleinimide was obtained in a yield of only 10.0 mole % based on the maleinamic methyl ester used as the raw material.

CONTROL 10

A maleinimide was produced from a maleinamic ester by following the procedure disclosed in JP-A-04-221,365 for the production of an N-substituted maleinimide from a corresponding N-substituted maleinamic ester, with necessary modifications.

In a three-neck flask having an inner volume of 200 ml and provided with a thermometers, a condenser furnished with a water separator, and a stirrer, 12.9 g (0.1 mole) of maleinamic methyl ester, 90 ml of methyl alcohol, and 0.8 g of sodium carbonate were placed and left reacting for removal of alcohol as stirred at room temperature (25° C.) for 3 hours. After the reaction was completed, the reaction solution was filtered to remove the catalyst. Then, the reaction solution was assayed by high-speed liquid chromatography to determine the amount of a maleinimide produced. The results indicate that the maleinimide was obtained in a yield of only 27.9 mole % based on the maleinamic methyl ester used as the starting material.

EXAMPLE 32

In a flask provided with a thermometer, a condenser furnished with a water separator, and a stirrer, 103.5 g (1.4 moles) of n-butanol, 69.0 g of toluene, and 4.6 g of concentrated sulfuric acid as a catalyst were placed and stirred and 23.0 (0.2 mole) of a maleinamic acid was added to the stirred mixture to form a slurry. The reaction consequently proceeding in the flask was continued for 5 hours with the internal temperature kept at 50° C. and the internal pressure at 85 mmHg while the water formed by the reaction was expelled meanwhile by distillation from the system. At the end of the reaction, the reaction solution was perfectly transparent. After the reaction was completed, the reaction solution was distilled under a reduced pressure to expel the catalyst and obtain a light yellow liquid. When this liquid was assayed by nuclear magnetic resonance, it was identified to be maleinamic n-butyl ester with a purity of 98% by weight. The liquid was assayed by high-speed liquid chromatography. The results indicate that the maleinamic n-butyl ester was obtained in a yield of 90.5 mole % based on the maleinamic acid used as the raw material.

EXAMPLES 33 TO 49

Various species of maleinamic n-butyl ester were produced by following the procedure of Example 32 while changing the molar ratio of charge of maleinamic acid as the raw material, n-butanol, and toluene as the azeotropic solvent to be charged. The results are shown in Table 6.

TABLE 6

| Example | Molar ratio of charge | | | Yield (mole % based on raw material) |
|---|---|---|---|---|
| | Raw material | Alcohol | Azeotropic solvent | |
| 33 | 1 | 7 | 3.75 | 90.5 |
| 34 | 1 | 5 | 1 | 90.1 |
| 35 | 1 | 5 | 5 | 88.2 |
| 36 | 1 | 5 | 8 | 78.2 |
| 37 | 1 | 7 | 1 | 92.1 |
| 38 | 1 | 7 | 5 | 89.0 |
| 39 | 1 | 7 | 8 | 80.7 |
| 40 | 1 | 10 | 1 | 93.1 |
| 41 | 1 | 10 | 5 | 92.6 |
| 42 | 1 | 10 | 8 | 79.9 |
| 43 | 1 | 14 | 3 | 92.0 |
| 44 | 1 | 14 | 5 | 91.4 |
| 45 | 1 | 17 | 2 | 93.5 |
| 46 | 1 | 17 | 1 | 94.0 |
| 47 | 1 | 18 | 1 | 94.3 |
| 48 | 1 | 23 | 16 | 96.2 |
| 49 | 1 | 23 | 8 | 96.9 |

EXAMPLES 50 TO 65

Various species of maleinamic n-butyl ester were produced by following the procedure of Example 32 while changing the molar ratio of charge of maleinamic acid as the raw material, 2-ethyl hexanol, and toluene as the azeotropic solvent. The results are shown in Table 7.

TABLE 7

| Example | Molar ratio of charge | | | Yield (mole % based on raw material) |
|---|---|---|---|---|
| | Raw material | Alcohol | Azeotropic solvent | |
| 50 | 1 | 5 | 1 | 88.2 |
| 51 | 1 | 5 | 5 | 85.6 |
| 52 | 1 | 5 | 8 | 75.3 |
| 53 | 1 | 7 | 1 | 90.1 |
| 54 | 1 | 7 | 5 | 87.9 |
| 55 | 1 | 7 | 8 | 76.3 |
| 56 | 1 | 10 | 1 | 91.8 |
| 57 | 1 | 10 | 5 | 89.5 |
| 58 | 1 | 10 | 8 | 78.2 |
| 59 | 1 | 14 | 3 | 88.3 |
| 60 | 1 | 14 | 5 | 87.3 |
| 61 | 1 | 17 | 2 | 89.2 |
| 62 | 1 | 17 | 1 | 89.3 |
| 63 | 1 | 18 | 1 | 90.1 |
| 64 | 1 | 23 | 16 | 90.2 |
| 65 | 1 | 23 | 8 | 92.4 |

EXAMPLES 66 TO 81

Various species of maleinamic n-butyl ester were produced by following the procedure of Example 32 while changing the molar ratio of charge of maleinamic acid as the raw material, ethanol, and toluene as the azeotropic solvent. The results are shown in Table 8.

TABLE 8

| Example | Molar ratio of charge | | | Yield (mole % based on raw material) |
|---|---|---|---|---|
| | Raw material | Alcohol | Azeotropic solvent | |
| 66 | 1 | 5 | 1 | 93.8 |
| 67 | 1 | 5 | 5 | 91.9 |
| 68 | 1 | 5 | 8 | 80.1 |
| 69 | 1 | 7 | 1 | 95.5 |
| 70 | 1 | 7 | 5 | 94.2 |
| 71 | 1 | 7 | 8 | 80.5 |
| 72 | 1 | 10 | 1 | 97.3 |
| 73 | 1 | 10 | 5 | 94.5 |
| 74 | 1 | 10 | 8 | 81.1 |
| 75 | 1 | 14 | 3 | 93.5 |
| 76 | 1 | 14 | 5 | 92.5 |
| 77 | 1 | 17 | 2 | 93.7 |
| 78 | 1 | 17 | 1 | 94.5 |
| 79 | 1 | 18 | 1 | 94.6 |
| 80 | 1 | 23 | 16 | 95.5 |
| 81 | 1 | 23 | 8 | 95.6 |

CONTROL 11

In a flask provided with a thermometer, a condenser furnished with a water separator, and a stirrer, 44.4 g (0.6 mole) of n-butanol, 180 ml of toluene, and 2.0 ml of concentrated sulfuric acid as a catalyst were placed and stirred and 23.0 g (0.2 mole) of a maleinamic acid was added to the stirred mixture to form a slurry. The reaction consequently proceeding in the flask was continued for 2 hours with the internal temperature set at 80° C. by lowering the internal pressure while the water formed by the reaction was expelled meanwhile by distillation from the system. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be maleinamic n-butyl ester with a purity of 60% by weight. It was assayed by high-speed liquid chromatography. The results indicate that the maleinamic n-butyl ester was obtained in a yield of 16.8 mole % based on the maleinamic acid used as the raw material.

CONTROLS 12 TO 17

Various species of maleinamic n-butyl ester were produced by following the procedure of Control 11 while changing the molar ratio of charge of maleinamic acid as the raw material, 2-ethyl hexanol, and toluene as the azeotropic solvent. The results are shown in Table 9.

TABLE 9

| Control | Molar ratio of charge | | | Yield (mole % based on raw material) |
|---|---|---|---|---|
| | Raw material | Alcohol | Azeotropic solvent | |
| 12 | 1 | 3 | 8.4 | 13.6 |
| 13 | 1 | 2 | 10 | 10.5 |
| 14 | 1 | 1 | 15 | 7.9 |
| 15 | 1 | 3 | 6 | 32.5 |
| 16 | 1 | 4 | 8 | 25.3 |
| 17 | 1 | 5 | 44 | 10.5 |

CONTROL 18

In a flask provided with a thermometer, a condenser furnished with a water separator, and a stirrer, 44.4 g (0.6 mole) of n-butanol, 180 ml of toluene, and 2.0 ml of concentrated sulfuric acid as a catalyst were placed and stirred and 23.0 g (0.2 mole) of a maleinamic acid was added to the stirred mixture to form a slurry. The reaction consequently proceeding in the flask was continued for 5 hours with the internal temperature set at 50° C. by lowering the internal pressure while the water formed by the reaction was expelled meanwhile by distillation from the system. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be maleinamic n-butyl ester with a purity of 75% by weight. It was assayed by high-speed liquid chromatography. The results indicate that the maleinamic n-butyl ester was obtained in a yield of 60.4 mole % based on the maleinamic acid used as the raw material.

CONTROLS 19 TO 24

Various species of maleinamic n-butyl ester were produced by following the procedure of Control 18 while changing the molar ratio of charge of a maleinamic acid as the raw material, ethanol, and toluene as the azeotropic solvent. The results are shown in Table 10.

TABLE 10

| Control | Molar ratio of charge | | | Yield (mole % based on raw material) |
|---|---|---|---|---|
| | Raw material | Alcohol | Azeotropic solvent | |
| 19 | 1 | 3 | 8.4 | 65.1 |
| 20 | 1 | 2 | 10 | 58.4 |
| 21 | 1 | 1 | 15 | 47.8 |
| 22 | 1 | 3 | 6 | 35.4 |
| 23 | 1 | 4 | 8 | 66.3 |

TABLE 10-continued

| Control | Molar ratio of charge | | | Yield (mole % based on raw material) |
|---|---|---|---|---|
| | Raw material | Alcohol | Azeotropic solvent | |
| 24 | 1 | 3 | 44 | 11.5 |

CONTROL 25

In a flask provided with a thermometer, a condenser furnished with a water separator, and a stirrer, 200 ml of n-butanol and 1.0 ml of concentrated sulfuric acid as a catalyst were placed and stirred and 23.0 g (0.2 mole) of a maleinamic acid was added to the stirred mixture to form a slurry. The reaction consequently proceeding in the flask was continued under a refluxing condition for one hour. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be maleinamic n-butyl ester with a purity of 75% by weight. It was assayed by high-speed liquid chromatography. The results indicate that the maleinamic n-butyl ester was obtained in a yield of 5.0 mole % based on the maleinamic acid used as the raw material.

CONTROLS 26 TO 28

Various species of maleinamic n-butyl ester were produced by following the procedure of Control 25 while changing the molar ratio of charge of maleinamic acid as the raw material, n-butanol, and the azeotropic solvent. The results are shown in Table 11.

TABLE 11

| Control | Molar ratio of charge | | | Yield (mole % based on raw material) |
|---|---|---|---|---|
| | Raw material | Alcohol | Azeotropic solvent | |
| 26 | 1 | 11 | 0 | 5.0 |
| 27 | 1 | 14 | 0 | 7.3 |
| 28 | 1 | 16 | 0 | 14.2 |

CONTROL 29

In a flask provided with a thermometer, a condenser furnished with a water separator, and a stirrer, 200 ml of n-butanol and 1.0 ml of concentrated sulfuric acid as a catalyst were placed and stirred and 23.0 g (0.2 mole) of a maleinamic acid was added to the stirred mixture to form a slurry. The reaction consequently proceeding in the flask was continued for 3 hours under a refluxing condition with the internal temperature set at 50° C. by lowering the internal pressure. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be maleinamic n-butyl ester with a purity of 80% by weight. It was further assayed by high-speed liquid chromatography. The results indicate that the maleinamic n-butyl ester was obtained in a yield of 62.0 mole % based on the maleinamic acid used as the raw material.

CONTROLS 30 AND 31

Various species of maleinamic n-butyl ester were produced by following the procedure of Control 29 while changing the molar ratio of charge of maleinamic acid as the raw material, n-butanol, and the azeotropic solvent. The results are shown in Table 12.

TABLE 12

| Control | Molar ratio of charge | | | Yield (mole % based on raw material) |
|---|---|---|---|---|
| | Raw material | Alcohol | Azeotropic solvent | |
| 30 | 1 | 14 | 0 | 65.3 |
| 31 | 1 | 16 | 0 | 69.7 |

The results of Examples 32 to 87 are diagrammatically represented in FIG. 1. In the diagram of FIG. 1, the part of an oblique line delineates the scope of this invention in terms of the relation of maleinamic acid, alcohol, and inert solvent.

EXAMPLE 88

In a flask provided with a thermometer, a condenser furnished with a water separator, and a stirrer, 103.5 g (1.4 moles) of n-butanol, 69.0 g of toluene, and 7.3 g of mono-n-butyl sulfate as a catalyst were placed and stirred and 23.0 g (0.2 mole) of a maleinamic acid was added to the stirred mixture to form a slurry. The reaction consequently proceeding in the flask was continued for 5 hours with the internal temperature kept at 50° C. and the internal pressure at 85 mmHg while the water formed by the reaction was expelled meanwhile by distillation from the system. At the end of the reaction, the reaction solution was perfectly transparent. After the reaction was completed, the reaction solution was distilled under a reduced pressure to expel the catalyst and obtain a light yellow liquid. When this liquid was assayed by nuclear magnetic resonance, it was identified to be maleinamic n-butyl ester with a purity of 95% by weight. The liquid was assayed by high-speed liquid chromatography. The results indicate that the maleinamic n-butyl ester was obtained in a yield of 88.7 mole % based on the maleinamic acid used as the raw material.

EXAMPLE 89

A maleinamic n-butyl ester was produced by following the procedure of Example 88 while changing the amount of the mono-n-butyl sulfate as the catalyst to 12.0 g. The results are shown in Table 13.

EXAMPLE 90

A maleinamic n-butyl ester was produced by following the procedure of Example 88 while changing the amount of the mono-n-butyl sulfate as the catalyst to 19.0 g. The results are shown in Table 13.

EXAMPLE 91

In a flask provided with a thermometer, a condenser furnished with a water separator, and a stirrer, 103.5 g (1.4 moles) of n-butanol, 69.0 g of toluene, and 10 g of a mixture of maleinamic acid with sulfuric acid as a catalyst were placed and stirred and 17.6 g of maleinamic acid was added to the stirred mixture to form a slurry. The reaction consequently proceeding in the flask was continued for 5 hours with the internal temperature kept at 50° C. and the internal pressure at 85 mmHg while the water formed by the reaction was expelled meanwhile by distillation from the system. At the end of the reaction, the reaction solution was perfectly transparent. After the reaction was completed, the reaction solution was distilled under a reduced pressure to expel the catalyst and obtain a light yellow liquid. When this liquid was assayed by nuclear magnetic resonance, it was identified to be maleinamic n-butyl ester with a purity of 98% by weight. The liquid was assayed by high-speed liquid chromatography. The results indicate that the maleinamic n-butyl ester was obtained in a yield of 93.5 mole % based on the maleinamic acid used as the raw material.

EXAMPLE 92

A maleinamic n-butyl ester was produced by following the procedure of Example 91 while changing the amount of the mixture of maleinamic acid with sulfuric acid to 26.0 g and the amount of maleinamic acid to 9.0 g. The results are shown in Table 13.

EXAMPLE 93

A maleinamic n-butyl ester was produced by following the procedure of Example 91 while changing the amount of the mixture of a maleinamic acid with sulfuric acid to 41.3 g and the amount of a maleinamic acid to 0.7 g. The results are shown in Table 13.

TABLE 13

| Example | Kind of catalyst | Amount of catalyst/total maleinamic acid (molar ratio) | Yield (mole % based on raw material) |
|---|---|---|---|
| 88 | ester | 0.24 | 88.7 |
| 89 | ester | 0.39 | 96.1 |
| 90 | ester | 0.62 | 87.9 |
| 91 | mixture | 0.24 | 93.5 |
| 92 | mixture | 0.61 | 95.9 |
| 93 | mixture | 0.97 | 91.2 |

EXAMPLES 94 AND 95

Various species of maleinamic n-butyl ester were produced by following the procedure of Examples 88 and 89 while using 103.5 g (2.3 moles) of ethanol as an alcohol, 69.0 g of hexane as an azeotropic solvent, and a mixture of monoethyl sulfuric ester, maleinamic acid, and sulfuric acid as a catalyst. The results are shown in Table 14.

TABLE 14

| Example | Kind of catalyst | Amount of catalyst/total maleinamic acid (molar ratio) | Yield (mole % based on raw material) |
|---|---|---|---|
| 94 | ester | 0.21 | 95.4 |
| 95 | mixture | 0.67 | 97.3 |

EXAMPLES 96 AND 97

Various species of maleinamic n-butyl ester were produced by following the procedure of Examples 88 and 89 while using 182.0 g (1.4 moles) of 2-ethyl hexanol as an alcohol, 69.0 g of toluene as an azeotropic solvent, and a mixture of mono-2-ethylhexyl sulfuric ester, maleinamic acid, and sulfuric acid as a catalyst. The results are shown in Table 15.

TABLE 15

| Example | Kind of catalyst | Amount of catalyst/total maleinamic acid (molar ratio) | Yield (mole % based on raw material) |
|---|---|---|---|
| 96 | ester | 0.31 | 84.6 |
| 97 | mixture | 0.87 | 83.9 |

EXAMPLE 98

In a flask provided with a thermometer, a condenser furnished with a water separator, and a stirrer, 103.5 g (1.4 moles) of n-butanol, 69.0 g of toluene, and 7.3 g of mono-n-butyl sulfuric ester as a catalyst were placed and stirred and 25.8 g (0.2 mole) of N-methyl maleinamic acid was added to the stirred mixture to form a slurry. The reaction consequently proceeding was carried out by following the procedure of Example 88, with the internal temperature of the flask set at 50° C. The reaction produced an N-methyl maleinamic ester in a yield of 86.4 mole % based on the N-methyl maleinamic acid as shown in Table 16.

EXAMPLE 99

In a flask provided with a thermometer, a condenser furnished with a water separator, and a stirrer, 103.5 g (1.4 moles) of n-butanol, 69.0 g of toluene, and 10.7 g of a mixture of an N-methyl maleinamic acid with sulfuric acid as a catalyst were placed and stirred and 19.7 g of an N-methyl maleinamic acid was added to the stirred mixture. The reaction which ensued was carried out by following the procedure of Example 88. The reaction produced an N-methyl maleinamic n-butyl ester in a yield of 90.3 mole % based on the whole of N-methyl maleinamic acid as shown in Table 16.

EXAMPLES 100 AND 101

Various species of N-methyl maleinamic ester were produced by following the procedure of Examples 98 and 99 while using ethanol as the alcohol, hexane as the azeotropic solvent, and a mixture of a monoethyl sulfuric ester, an N-methyl maleinamic acid, and sulfuric acid as the catalyst. The results are shown in Table 16.

EXAMPLES 102 AND 103

Various species of N-methyl maleinamic ester were produced by following the procedure of Examples 98 and 99 while using 2-ethylhexyl alcohol as the alcohol, toluene as the azeotropic solvent, and a mixture of a mono-2-ethylhexyl sulfuric ester, an N-methyl maleinamic acid, and sulfuric acid as the catalyst. The results are shown in Table 16.

TABLE 16

| Example | Kind of catalyst | Amount of catalyst/total maleinamic acid (molar ratio) | Yield (mole % based on raw material) |
|---|---|---|---|
| 98 | ester | 0.24 | 90.6 |
| 99 | mixture | 0.24 | 91.1 |

TABLE 16-continued

| Example | Kind of catalyst | Amount of catalyst/total maleinamic acid (molar ratio) | Yield (mole % based on raw material) |
|---|---|---|---|
| 100 | ester | 0.38 | 93.3 |
| 101 | mixture | 0.72 | 94.1 |
| 102 | ester | 0.27 | 86.5 |
| 103 | mixture | 0.55 | 84.6 |

EXAMPLES 104 TO 109

Various species of N-methyl maleinamic ester were produced by following the procedure of Examples 98 to 103 while using 34.2 g (0.1 mole) of a N-butyl maleinamic acid as a raw material and a mixture of the monoalkyl sulfuric ester of the alcohol to be used, an N-butyl maleinamic acid, and sulfuric acid as the catalyst. The results are shown in Table 17.

TABLE 17

| Example | Kind of catalyst | Amount of catalyst/total maleinamic acid (molar ratio) | Yield (mole % based on raw material) |
|---|---|---|---|
| 104 | ester | 0.24 | 89.5 |
| 105 | mixture | 0.24 | 87.7 |
| 106 | ester | 0.88 | 84.4 |
| 107 | mixture | 0.18 | 82.9 |
| 108 | ester | 0.36 | 80.5 |
| 109 | mixture | 0.33 | 81.6 |

EXAMPLES 110 TO 115

Various species of N-methyl maleinamic ester were produced by following the procedure of Examples 104 to 109 while using 45.4 g (0.2 mole) of an N-2-ethylhexyl maleinamic acid as a raw material and a mixture of the monoalkyl sulfuric ester of the alcohol to be used, an N-2-ethylhexyl maleinamic acid, and sulfuric acid as the catalyst. The results are shown in Table 18.

TABLE 18

| Example | Kind of catalyst | Amount of catalyst/total maleinamic acid (molar ratio) | Yield (mole % based on raw material) |
|---|---|---|---|
| 110 | ester | 0.24 | 80.3 |
| 111 | mixture | 0.24 | 79.8 |
| 112 | ester | 0.66 | 80.5 |
| 113 | mixture | 0.57 | 82.1 |
| 114 | ester | 0.43 | 78.7 |
| 115 | mixture | 0.33 | 77.6 |

CONTROL 32

In a flask provided with a thermometer, a condenser furnished with a water separator, and a stirrer, 44.4 g (0.6 mole) of n-butanol, 180 ml of toluene, and 2.0 ml of concentrated sulfuric acid as a catalyst were placed and stirred and 23.0 g (0.2 mole) of a maleinamic acid was added to the stirred mixture to form a slurry. The reaction consequently proceeding in the flask was continued for 2 hours with the internal temperature set at 80° C. by lowering the internal pressure while the water formed by the reaction was expelled meanwhile by distillation from the system. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be a maleinamic n-butyl ester with a purity of 60% by weight. It was assayed by high-speed liquid chromatography. The results indicate that the maleinamic n-butyl ester was obtained in a yield of 16.8 mole % based on the maleinamic acid used as the raw material.

CONTROL 33

In a flask provided with a thermometer, a condenser furnished with a water separator, and a stirrer, 44.4 g (0.6 mole) of n-butanol, 180 ml of toluene, and 2.0 ml of concentrated sulfuric acid as a catalyst were placed and stirred and 23.0 g (0.2 mole) of a maleinamic acid was added to the stirred mixture to form a slurry. The reaction consequently proceeding in the flask was continued for 5 hours with the internal temperature set at 50° C. by lowering the internal pressure while the water formed by the reaction was expelled meanwhile by distillation from the system. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be a maleinamic n-butyl ester with a purity of 75% by weight. It was assayed by high-speed liquid chromatography. The results indicate that the maleinamic n-butyl ester was obtained in a yield of 60.4 mole % based on the maleinamic acid used as the raw material.

CONTROL 34

In a flask provided with a thermometer, a condenser furnished with a water separator, and a stirrer, 200 ml of n-butanol and 1.0 ml of concentrated sulfuric acid as a catalyst were placed and stirred and 23.0 g (0.2 mole) of a maleinamic acid was added to the stirred mixture to form a slurry. The reaction consequently proceeding in the flask was continued under a refluxing condition for one hour. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be a maleinamic n-butyl ester with a purity of 75% by weight. It was assayed by high-speed liquid chromatography. The results indicate that the maleinamic n-butyl ester was obtained in a yield of 5.0 mole % based on the maleinamic acid used as the raw material.

CONTROL 35

In a flask provided with a thermometer, a condenser furnished with a water separator, and a stirrer, 200 ml of n-butanol and 1.0 ml of concentrated sulfuric acid as a catalyst were placed and stirred and 23.0 g (0.2 mole) of a maleinamic acid was added to the stirred mixture to form a slurry. The reaction consequently proceeding in the flask was continued for 3 hours under a refluxing condition with the internal temperature set at 50° C. by lowering the internal pressure. At the end of the reaction, the reaction solution was still in the form of a slurry. After the reaction was completed, the reaction solution was filtered. The filtrate was distilled under a reduced pressure to expel the solvent and obtain a light yellow liquid. When this liquid was assayed by nuclear magnetic resonance, it was identified to be a maleinamic n-butyl ester with a purity of 80% by weight. It was further assayed by high-speed liquid chromatography. The results indicate that the maleinamic n-butyl ester was obtained in a yield of 62.0 mole % based on the maleinamic acid used as the raw material.

EXAMPLE 116

An autoclave having an inner volume of 5,000 ml and provided with a gas inlet tube, a thermometer, and a stirrer was charged with 2,941 g of a toluene 10 wt % maleic anhydride solution. The autoclave, after having the empty space part thereof charged with 82.8 liters of ammonia gas at 23° C., was tightly sealed. When the toluene solution was stirred at a temperature of 35° C. for 2 hours, the reaction solution consequently formed assumed the form of a slurry. After the stirring was completed, the reaction solution was heated to a temperature of 60° C. and further stirred for 2 hours. After the stirring was completed, the autoclave was opened and the reaction solution therein was quickly sampled. The sample was assayed by gas chromatography and nuclear magnetic resonance. The results indicate that the reaction produced a maleinamic acid in a yield of 97.4 mole % based on the maleic anhydride.

In the autoclave, after the gas filling the empty space part thereof was displaced with nitrogen gas, 960 g of methyl alcohol and 345 g of a strongly acidic ion-exchange resin having a water content of 10% by weight (produced by Mitsubishi Chemical Co., Ltd. and marketed under trademark designation of "DIAION-PK216") were placed and stirred at 40° C. for 2 hours to effect a reaction of esterification. At the end of the stirring, the reaction solution was perfectly transparent. Subsequently, the reaction solution was filtered to remove the ion-exchange resin. The filtrate was distilled under a reduced pressure to expel the solution and obtain 382 g of a light yellow transparent liquid. When this liquid was assayed by gas chromatography and nuclear magnetic resonance, it was identified to be a maleinamic methyl ester with a purity of 93.8% by weight. The results indicate that the maleinamic methyl ester was obtained in a yield of 92.6 mole % based on the maleic anhydride as the raw material.

EXAMPLE 117

An autoclave having an inner volume of 5,000 ml and provided with a gas inlet tube, a thermometer, and a stirrer was charged with 2,941 g of a toluene 10 wt % maleic anhydride solution. The autoclave, after having the empty space part thereof charged with 72.8 liters of ammonia gas at 23° C., was tightly sealed. When the toluene solution was stirred at a temperature of 45° C. for 2 hours, the reaction solution consequently formed assumed the form of a slurry. After the stirring was completed, the reaction solution was heated to a temperature of 60° C. and further stirred for 2 hours. After the stirring was completed, the autoclave was opened and the reaction solution therein was quickly sampled. The sample was assayed by gas chromatography and nuclear magnetic resonance. The results indicate that the reaction produced a maleinamic acid in a yield of 98.3 mole % based on the maleic anhydride.

In the autoclave, after the gas filling the empty space part thereof was displaced with nitrogen gas, 1,440 g of n-propyl alcohol and 230 g of a strongly acidic ion-exchange resin having a water content of 10% by weight (produced by Mitsubishi Chemical Co., Ltd. and marketed under trademark designation of "DIAION-PK216") were placed and stirred at 60° C. for 2 hours to effect a reaction of esterification. At the end of the stirring, the reaction solution was perfectly transparent. Subsequently, the reaction solution was filtered to remove the ion-exchange resin. The filtrate was distilled under a reduced pressure to expel the solution and obtain 454 g of a light yellow transparent liquid. When this liquid was assayed by gas chromatography and nuclear magnetic resonance, it was identified to be a maleinamic n-propyl ester with a purity of 90.2% by weight. The results indicate that the maleinamic n-propyl ester was obtained in a yield of 86.9 mole % based on the maleic anhydride as the raw material.

EXAMPLE 118

An autoclave having an inner volume of 5,000 ml and provided with a gas inlet tube, a water separator, a thermometer, and a stirrer was charged with 2,941 g of a toluene 10 wt % maleic anhydride solution. The autoclave, after having the empty space part thereof charged with 71.5 liters of ammonia gas at 23° C., was tightly sealed. When the toluene solution was stirred at a temperature of 35° C. for 2 hours, the reaction solution consequently formed assumed the form of a slurry. After the stirring was completed, the reaction solution was heated to a temperature of 60° C. and further stirred for 2 hours. After the stirring was completed, the autoclave was opened and the reaction solution therein was quickly sampled. The sample was assayed by gas chromatography and nuclear magnetic resonance. The results indicate that the reaction produced a maleinamic acid in a yield of 98.6 mole % based on the maleic anhydride.

In the autoclave, after the gas filling the empty space part thereof was displaced with nitrogen gas, 902 g of n-propyl alcohol and 20 g of concentrated sulfuric acid were placed and stirred under a refluxing condition for 2 hours. At the end of the stirring, the reaction solution was perfectly transparent. Subsequently, the reaction solution was washed with 100 ml of purified water to separate an aqueous layer and remove sulfuric acid. The remaining solution was distilled under a reduced pressure to remove an organic layer and obtain 429 g of a light yellow transparent liquid. When this liquid was assayed by gas chromatography and nuclear magnetic resonance, it was identified to be a maleinamic n-propyl ester with a purity of 88.2 by weight. The results indicate that the maleinamic methyl ester was obtained in a yield of 80.3 mole % based on the maleic anhydride as the raw material.

EXAMPLE 119

An autoclave having an inner volume of 5,000 ml and provided with a gas inlet tube, a water separating tube, a thermometer, and a stirrer was charged with 2,941 g of a toluene 10 wt % maleic anhydride solution. The autoclave, after having the empty space part thereof charged with 72.8 liters of ammonia gas at 23° C., was tightly sealed. When the toluene solution was stirred at a temperature of 35° C. for 2 hours, the reaction solution consequently formed assumed the form of a slurry. After the stirring was completed, the autoclave was opened and the reaction solution therein was quickly sampled. The sample was assayed by gas chromatography and nuclear magnetic resonance. The results indicate that the reaction produced a maleinamic acid in a yield of 97.9 mole % based on the maleic anhydride.

In the autoclave, after the gas filling the empty space part thereof was displaced with nitrogen gas, 1,803 g of n-propyl alcohol and 345 g of a strongly acidic ion-exchange resin having a water content of 10% by weight (produced by Mitsubishi Chemical Co., Ltd. and marketed under trademark designation of "DIAION-PK216") were placed and stirred under a refluxing condition for 2 hours. At the end of the stirring, the reaction solution was perfectly transparent. Subsequently, the reaction solution was filtered to remove the ion-exchange resin. The filtrate was distilled under a reduced pressure to expel the solution and obtain 445 g of a light yellow transparent liquid. When this liquid was assayed by gas chromatography and nuclear magnetic resonance, it was identified to be a maleinamic n-propyl ester with a purity of 90.3% by weight. The results indicate that the maleinamic n-propyl ester was obtained in a yield of 85.3 mole % based on the maleic anhydride as the raw material.

CONTROL 36

A separable flask having an inner volume of 5,000 ml and provided with an ammonia inlet tube, a dropping funnel, a thermometer, and a stirrer was charged with 2,941 g of a toluene 10 wt % maleic anhydride solution. When ammonia gas was blown into the solution at room temperature (23° C.) at a flow rate of 274 ml/min, the ammonia gas orifice was blocked after 5 minutes' blowing. The passage of ammonia gas was suspended and then the orifice and the vicinity thereof were cleared of deposited crystals before the passage of ammonia gas was restarted. A total of 72.8 liters of ammonia was introduced into the solution by repeating this procedure ten-odd times. The reaction solution was in the form of a slurry. After the introduction of ammonia gas was completed, the reaction solution was heated to 60° C. and then stirred continuously for 2 hours. When the stirring was completed, the reaction solution was quickly sampled and assayed by gas chromatography and nuclear magnetic resonance. The results indicate that maleinamic acid was produced in a yield of 69.2 mole % based on the maleic anhydride.

Subsequently, the reaction solution held in the flask and 960 g of methyl alcohol and 345 g of a strongly acidic ion-exchange resin having a water content of 10% by weight (produced by Mitsubishi Chemical Co., Ltd. and marketed under trademark designation of "DIAION-PK216") added thereto were stirred continuously for 2 hours at 40° C. The reaction solution was still in the form of a slurry. It was filtered to separate the ion-exchange resin and white solid lumps from the reaction solution. The filtrate was distilled under a reduced pressure to remove the solution and obtain 225 g of a light yellow transparent liquid. When this liquid was assayed by gas chromatography and nuclear magnetic resonance, it was identified to be a maleinamic methyl ester with a purity of 78% by weight. The results indicate that the maleinamic methyl ester was obtained in a yield of 45.3 mole % based on the maleic anhydride used as the raw material.

EXAMPLE 120

A separable flask having an inner volume of 5,000 ml and provided with an ammonia gas inlet tube, a dropping funnel, a thermometer, and a stirrer was charged with 588.2 g of toluene solution. The dropping funnel was charged with 2,941 g of a toluene 10 wt % maleic anhydride solution. The toluene solution of maleic anhydride was added dropwise at room temperature (23° C.) over a period of 4 hours and 26 minutes and, at the same time, ammonia gas was blown into the toluene solution in the flask at a flow rate of 274 ml/min. The reaction solution then assumed the form of a slurry. In this while, the concentration of maleic anhydride in the reaction solution was 3% by weight. After the dropwise addition was completed, the passage of ammonia gas was suspended and the reaction solution was heated to a temperature of 60° C. and stirred continuously for 2 hours. The stirring was temporarily suspended and part of the reaction solution was extracted as a sample and assayed. The results indicate that a maleinamic acid was produced in a yield of 98.5 mole % based on the maleic anhydride used as the raw material.

The reaction solution held in the flask and 960 g of methyl alcohol and 345 g of a strongly acidic ion-exchange resin having a water content of 10% by weight (produced by Mitsubishi Chemical Co., Ltd. and marketed under trademark designation of. "DIAION-PK216") added thereto during the temporary suspension of the stirring mentioned above were subsequently stirred at 40° C. for 2 hours. The reaction solution was completely transparent. It was then filtered to separate the ion-exchange resin therefrom. The filtrate was distilled under a reduced pressure to remove the solvent and obtain 385 g of a light yellow transparent liquid. When this liquid was assayed by gas chromatography and nuclear magnetic resonance, it was identified to be a maleinamic methyl ester with a purity of 92% by weight. The results indicate that the maleinamic methyl ester was obtained in a yield of 91.5 mole % based on the maleic anhydride used as the raw material.

EXAMPLE 121

A separable flask having an inner volume of 5,000 ml and provided with an ammonia gas inlet tube, a dropping funnel, a thermometer, and a stirrer was charged with 588.2 g of toluene, The dropping funnel was charged with 2,941 g of a toluene 10 wt % maleic anhydride solution. The toluene solution of maleic anhydride was added dropwise at room temperature (23° C.) over a period of 4 hours and 52 minutes and, at the same time, ammonia gas was blown into the toluene solution in the flask at a flow rate of 250 ml/min. The reaction solution then assumed the form of a slurry. In this while, the concentration of maleic anhydride in the reaction solution was 2% by weight. After the dropwise addition was completed, the passage of ammonia gas was suspended and the reaction solution was heated to a temperature of 60° C. and stirred continuously for 2 hours.

The stirring was temporarily suspended. The reaction solution held then in the flask and 1,803 g of n-propyl alcohol and 345 g of the same strongly acidic ion-exchange resin as used in Example 120 added thereto during the temporary suspension of the stirring were subsequently stirred at 60° C. for 2 hours. The reaction solution was completely transparent. It was then filtered to separate the ion-exchange resin therefrom. The filtrate was distilled under a reduced pressure to remove the solvent and obtain 465 g of a light yellow transparent liquid. When this liquid was assayed by gas chromatography and nuclear magnetic resonance, it was identified to be a maleinamic methyl ester with a purity of 90% by weight.

The results indicate that the maleinamic methyl ester was obtained in a yield of 88.9 mole % based on the maleic anhydride used as the raw material.

EXAMPLE 122

A separable flask having an inner volume of 5,000 ml and provided with an ammonia gas inlet tube, a dropping funnel, a thermometer, a condenser furnished with a water separating tube, and a stirrer was charged with 588.2 g of toluene. The dropping funnel was charged with 2,941 g of a toluene 10 wt % maleic anhydride solution. The toluene solution of maleic anhydride was added dropwise at room temperature (23° C.) over a period of 3 hours and, at the same time, ammonia gas was blown into the toluene solution in the flask at a flow rate of 405 ml/min. The reaction solution then assumed the form of a slurry. In this while, the concentration of the maleic anhydride in the reaction solution was 5% by weight. After the dropwise addition was completed, the passage of ammonia gas was suspended and the reaction solution was heated to a temperature of 60° C. and stirred continuously for 2 hours.

The stirring was temporarily suspended. The reaction solution held then in the flask and 902 g of n-propyl alcohol and 20 g of concentrated sulfuric acid added thereto during the temporary suspension of the stirring were subsequently stirred under a refluxing condition for 2 hours. The reaction solution was completely transparent. It was then washed with 100 ml of purified water to separate a water layer and remove sulfuric acid. The remaining reaction solution was distilled under a reduced pressure to remove an organic layer and obtain 432 g of a light yellow transparent liquid. When this liquid was assayed by gas chromatography and nuclear magnetic resonance, it was identified to be a maleinamic n-propyl ester with a purity of 87% by weight. The results indicate that the maleinamic n-propyl ester was obtained in a yield of 79.8 mole % based on the maleic anhydride used as the raw material.

EXAMPLE 123

A separable flask having an inner volume of 5,000 ml and provided with an ammonia gas inlet tube, a dropping funnel, a thermometer, a condenser furnished with a water separating tube, and a stirrer was charged with 588.2 g of toluene. The dropping funnel was charged with 2,941 g of a toluene 10 wt % maleic anhydride solution. The toluene solution of maleic anhydride was added dropwise at room temperature (23° C.) over a period of 4 hours 26 minutes and, at the same time, ammonia gas was blown into the toluene solution in the flask at a flow rate of 274 ml/min. The reaction solution then assumed the form of a slurry. In this while, the concentration of the maleic anhydride in the reaction solution was 3% by weight. After the dropwise addition was completed, the passage of ammonia gas was suspended and the reaction solution was heated to a temperature of 60° C. and stirred continuously for 2 hours.

The stirring was temporarily suspended. The reaction solution held then in the flask and 1,803 g of n-propyl alcohol and 345 g of a strongly acidic ion-exchange resin having a water content of 10% by weight (produced by Mitsubishi Chemical Co., Ltd. and marketed under trademark designation of "DIAION-PK201") added thereto during the temporary suspension of the stirring were subsequently stirred under a refluxing condition for 2 hours. The reaction solution was completely transparent. It was then filtered to remove the ion-exchange resin therefrom. The filtrate was distilled under a reduced pressure to remove the solvent and obtain 472 g of a light yellow transparent liquid. When this liquid was assayed by gas chromatography and nuclear magnetic resonance, it was identified to be a maleinamic n-propyl ester with a purity of 92% by weight. The results indicate that the maleinamic n-propyl ester was obtained in a yield of 92.2 mole % based on the maleic anhydride used as the raw material.

CONTROL 37

A separable flask having an inner volume of 5,000 ml and provided with an ammonia inlet tube, a dropping funnel, a thermometer, and a stirrer was charged with 2,941 g of a toluene 10 wt % maleic anhydride solution. When ammonia gas was blown into the solution at room temperature (23° C.) at a flow rate of 274 ml/min, the ammonia gas orifice was blocked after 5 minutes' blowing. The passage of ammonia gas was suspended and then the orifice and the vicinity thereof were cleared of deposited crystals before the passage of ammonia gas was restarted. A total of 72.8 liters of ammonia was introduced into the solution by repeating this procedure ten-odd times. The reaction solution was in the form of a slurry. After the introduction of ammonia gas was completed, the reaction solution was heated to 60° C. and then stirred continuously for 2 hours. When the stirring was completed, the reaction solution was quickly sampled and assayed by gas chromatography and nuclear magnetic resonance. The results indicate that a maleinamic acid was produced in a yield of 69.2 mole % based on the maleic anhydride.

Subsequently, the reaction solution held in the flask and 960 g of methyl alcohol and 345 g of a strongly acidic ion-exchange resin having a water content of 10% by weight (produced by Mitsubishi Chemical Co., Ltd. and marketed under trademark designation of "DIAION-PK216") added thereto were stirred continuously for 2 hours at 40° C. The reaction solution was still in the form of a slurry. It was filtered to separate the ion-exchange resin and white solid lumps from the reaction solution. The filtrate was distilled under a reduced pressure to remove the solution and obtain 225 g of a light yellow transparent liquid. When this liquid was assayed by gas chromatography and nuclear magnetic resonance, it was identified to be a maleinamic methyl ester with a purity of 78% by weight. The results indicate that the maleinamic methyl ester was obtained in a yield of 45.3 mole % based on the maleic anhydride used as the raw material.

EXAMPLE 124

A separable flask having an inner volume of 5,000 ml and provided with an ammonia inlet tube, a dropping funnel, a thermometer, and a stirrer was charged with 588.2 g of toluene and kept at a temperature of 35° C. Meanwhile, the dropping funnel was charged with 2,941 g of a toluene 10 wt % maleic anhydride solution.

First, ammonia gas was blown into the toluene solution in the flask at a flow rate of 280 ml/min for 5 minutes. Then, the toluene solution of maleic anhydride was added dropwise over a period of 4 hours and 26 minutes into the toluene in the flask while the blowing of ammonia gas was continued at the same flow rate as mentioned above. The reaction solution then assumed the form of a slurry. In this while, the ammonia concentration in the reaction solution was 0.04% by weight.

After the dropwise addition was completed, the passage of ammonia gas was stopped and the reaction solution was heated to a temperature of 60° C. and stirred continuously for 2 hours. The stirring was temporarily suspended and part of the reaction solution was extracted as a sample and assayed. The results indicate that the reaction produced a maleinamic acid in a yield of 98.6 mole % based on the maleic anhydride used as the raw material.

The reaction solution in the flask and 960 g of methyl alcohol and 345 g of a strongly acidic ion-exchange resin having a water content of 10% by weight (produced by Mitsubishi Chemical Co., Ltd. and marketed under trademark designation of "DIAION-PK216") added thereto during the temporary suspension of stirring mentioned above were stirred together continuously at 40° C. for 2 hours. The reaction solution grew completely transparent. It was filtered to remove the ion-exchange resin therefrom. The filtrate was distilled under a reduced pressure to expel the solvent and obtain 383 g of a light yellow transparent liquid. When this liquid was assayed by gas chromatography and nuclear magnetic resonance, it was identified to be a maleinamic methyl ester with a purity of 93% by weight. The results indicate that the maleinamic methyl ester was obtained in a yield of 92.0 mole % based on the maleic anhydride used as the raw material.

EXAMPLE 125

A separable flask having an inner volume of 5,000 ml and provided with an ammonia inlet tube, a dropping funnel, a thermometer, and a stirrer was charged with 588.2 g of toluene and kept at a temperature of 35° C. Meanwhile, the dropping funnel was charged with 2,941 g of a toluene 10 wt % maleic anhydride solution.

First, ammonia gas was blown into the toluene solution in the flask at a flow rate of 276 ml/min for 5 minutes. Then, the toluene solution of maleic anhydride was added dropwise over a period of 4 hours and 26 minutes into the toluene in the flask while the blowing of ammonia gas was continued at the same flow rate as mentioned above. The reaction solution then assumed the form of a slurry. In this while, the ammonia concentration in the reaction solution was 0.02% by weight.

After the dropwise addition was completed, the passage of ammonia gas was stopped and the reaction solution was heated to a temperature of 60° C. and stirred continuously for 2 hours. The stirring was temporarily suspended and part of the reaction solution was extracted as a sample and assayed. The results indicate that the reaction produced a maleinamic acid in a yield of 98.6 mole % based on the maleic anhydride used as the raw material.

The reaction solution in the flask and 1,803 g of n-propyl alcohol and 345 g of a strongly acidic ion-exchange resin having a water content of 10% by weight (produced by Mitsubishi Chemical Coo, Ltd. and marketed under trademark designation of "DIAION-PK216") added thereto during the temporary suspension of stirring mentioned above were stirred together continuously at 40° C. for 2 hours. The reaction solution grew completely transparent. It was filtered to remove the ion-exchange resin therefrom. The filtrate was distilled under a reduced pressure to expel the solvent and obtain 462 g of a light yellow transparent liquid. When this liquid was assayed by gas chromatography and nuclear magnetic resonance, it was identified to be a maleinamic n-propyl ester with a purity of 91% by weight. The results indicate that the maleinamic n-propyl ester was obtained in a yield of 90.2 mole % based on the maleic anhydride used as the raw material.

EXAMPLE 126

A separable flask having an inner volume of 5,000 ml and provided with an ammonia inlet tube, a dropping funnel, a thermometer, and a stirrer was charged with 588.2 g of toluene and kept at a temperature of 35° C. Meanwhile, the dropping funnel was charged with 2,941 g of a toluene 10 wt % maleic anhydride solution.

First, ammonia gas was blown into the toluene solution in the flask at a flow rate of 283 ml/min for 5 minutes. Then, the toluene solution of maleic anhydride was added dropwise over a period of 4 hours and 27 minutes into the toluene in the flask while the blowing of ammonia gas was continued at the same flow rate as mentioned above. The reaction solution then assumed the form of a slurry. In this while, the ammonia concentration in the reaction solution was 0.02% by weight.

After the dropwise addition was completed, the passage of ammonia gas was stopped and the reaction solution was heated to a temperature of 60° C. and stirred continuously for 2 hours. The stirring was temporarily suspended and part of the reaction solution was extracted as a sample and assayed. The results indicate that the reaction produced a maleinamic acid in a yield of 99.0 mole % based on the maleic anhydride used as the raw material.

The reaction solution in the flask and 1,803 g of n-propyl alcohol and 20 g of concentrated sulfuric acid added thereto during the temporary suspension of stirring mentioned above were stirred together continuously under a refluxing condition for 2 hours. The reaction solution grew completely transparent. It was filtered to remove the concentrated sulfuric acid therefrom. The filtrate was distilled under a reduced pressure to expel the solvent and obtain 441 g of a light yellow transparent liquid. When this liquid was assayed by gas chromatography and nuclear magnetic resonance, it was identified to be a maleinamic n-propyl ester with a purity of 89% by weight. The results indicate that the maleinamic n-propyl ester was obtained in a yield of 83.3 mole % based on the maleic anhydride used as the raw material.

EXAMPLE 127

A separable flask having an inner volume of 5,000 ml and provided with an ammonia inlet tube, a dropping funnel, a thermometer, and a stirrer was charged with 588.2 g of toluene and kept at a temperature of 35° C. Meanwhile, the dropping funnel was charged with 2,941 g of a toluene 10 wt % maleic anhydride solution.

First, ammonia gas was blown into the toluene solution in the flask at a flow rate of 281 ml/min for 5 minutes. Then, the toluene solution of maleic anhydride was added dropwise over a period of 4 hours and 28 minutes into the toluene in the flask while the blowing of ammonia gas was continued at the same flow rate as mentioned above. The reaction solution then assumed the form of a slurry. In this while, the ammonia concentration in the reaction solution was 0.03% by weight. After the dropwise addition was completed, the passage of ammonia gas was stopped and the reaction solution was heated to a temperature of 60° C. and stirred continuously for 2 hours. The stirring was temporarily suspended and part of the reaction solution was extracted as a sample and assayed. The results indicate that the reaction produced a maleinamic acid in a yield of 99.0 mole % based on the maleic anhydride used as the raw material.

The reaction solution in the flask and 1,803 g of n-propyl alcohol and 345 g of a strongly acidic ion-exchange resin having a water content of 10% by weight (produced by Mitsubishi Chemical Co., Ltd. and marketed under trademark designation of "DIAION-PK216") added thereto during the temporary suspension of stirring mentioned above were stirred together continuously at 60° C. for 2 hours. The reaction solution grew completely transparent. It was filtered to remove the ion-exchange resin therefrom. The filtrate was distilled under a reduced pressure to expel the solvent and obtain 470 g of a light yellow transparent liquid. When this liquid was assayed by gas chromatography and nuclear magnetic resonance, it was identified to be a maleinamic n-propyl ester with a purity of 93% by weight. The results indicate that the maleinamic n-propyl ester was obtained in a yield of 92.8 mole % based on the maleic anhydride used as the raw material.

CONTROL 38

A separable flask having an inner volume of 5,000 ml and provided with an ammonia inlet tube, a dropping funnel, a thermometer, and a stirrer was charged with 2,941 g of a toluene 10 wt % maleic anhydride solution. When ammonia gas was blown into the solution at room temperature (23° C.) at a flow rate of 274 ml/min, the ammonia gas orifice was blocked after 5 minutes' blowing. The passage of ammonia gas was suspended and then the orifice and the vicinity thereof were cleared of deposited crystals before the passage of ammonia gas was restarted. A total of 72.8 liters of ammonia was introduced into the solution by repeating this procedure several times. The reaction solution was in the form of a slurry. After the introduction of ammonia gas was completed, the reaction solution was heated to 60° C. and then stirred continuously for 2 hours. When the stirring was completed, the reaction solution was quickly sampled and assayed by gas chromatography and nuclear magnetic resonance. The results indicate that a maleinamic acid was produced in a yield of 69.2 mole % based on the maleic anhydride.

Subsequently, the reaction solution held in the flask and 960 g of methyl alcohol and 345 g of a strongly acidic ion-exchange resin having a water content of 10% by weight (produced by Mitsubishi Chemical Co., Ltd. and marketed under trademark designation of "DIAION-PK216") added thereto were stirred continuously for 2 hours at 40° C. The reaction solution was still in the form of a slurry. It was filtered to separate the ion-exchange resin and white solid lumps from the reaction solution. The filtrate was distilled under a reduced pressure to remove the solution and obtain 225 g of a light yellow transparent liquid. When this liquid was assayed by gas chromatography and nuclear magnetic resonance, it was identified to be a maleinamic methyl ester with a purity of 78% by weight. The results indicate that the maleinamic methyl ester was obtained in a yield of 45.3 mole % based on the maleic anhydride used as the raw material.

INDUSTRIAL APPLICABILITY

This invention, in producing an N-unsubstituted maleinimide by subjecting a corresponding N-unsubstituted maleinamic ester to a ring-closing alcohol-removing reaction for conversion into an imide, permits the maleinimide to be produced expeditiously in a high yield with high selectivity by using an acid catalyst or a mono(cyclo)alkyl sulfuric ester in the reaction as described above.

It can produce the maleinimide in a high yield by adjusting the alcohol concentration in the reaction solution at a low level thereby curbing the possible occurrence of complicated secondary reactions due to the formed alcohol. Since the alcohol-removing reaction in this invention proceeds very easily as compared with the treatment of dehydrocyclization by use of the well-known dehydrating agent, the method of this invention permits the maleinimide to be produced with high efficiency as compared with the conventional method using the dehydrating agent. The method of this invention enjoys a generous saving in the cost of production because the maleinimide obtained by this method has a very high purity and obviates the necessity for special treatment for purification. Thus, the method of this invention enables the maleinimide to be produced at a low cost.

Further, according to the method of this invention, since the alcohol-removing reaction is carried out while the highly reactive maleinimide produced by the reaction is continuously extracted by distillation from the reaction system, such secondary reactions as the reaction between a maleinamic ester as the st arting material and the maleinimide as the product of reaction and the homopolymerization of the maleinimide itself can be curbed and the maleinimide can be produced in a high yield. Since the alcohol-removing reaction in this invention proceeds very easily as compared with the reaction of dehydrocyclization using the well-known dehydrating agent, the method of this invention enables the maleinimide to be produced with greater efficiency than the conventional method using the dehydrating agent.

This invention is also directed to a method for the production of an N-unsubstituted or N-substituted maleinamic ester represented by the general formula (6) by the reaction of an N-unsubstituted or N-substituted maleinamic acid represented by the general formula (3) with an alcohol represented by the general formula (4) in an inert solvent in the presence of a mixture of a maleinamic acid with an acid catalyst or a mono(cyclo)alkyl sulfuric ester. Thus, it permits a corresponding maleinamic ester to be produced expeditiously in a high yield with high selectivity.

This invention is capable of curving sudden formation and separation of a maleinamic acid and, therefore, enabling the maleinamic acid to be produced in a high yield with high purity. It further precludes the blockage of the neighborhood of the orifice ejecting ammonia gas into the reaction solution and consequently allows smooth passage of ammonia gas into the reaction solution and permits the maleinamic acid to be stably produced.

Since this invention curbs sudden formation and separation of the maleinamic acid, it can produce the maleinamic acid in a high yield with high purity. Further, by precluding the blockage of the neighborhood of the orifice ejecting ammonia gas into the reaction solution and consequently ensuring smooth passage of the ammonia gas into the reaction solution, this invention enables the production of the maleinamic acid to proceed stably.

According to this invention, since the reaction of the maleic anhydride with ammonia proceeds mainly near the surface of the reaction solution, no unaltered ammonia is any longer suffered to be contained in the formed malainamic acid and the maleinamic acid can be produced in a high yield with high purity. According to this invention, since the maleinamic acid is obtained in a high yield with high purity, the reaction solution containing this maleinamic acid can be used in its unaltered form, namely without being refined by removal of the maleinamic acid therefrom, for the purpose of being combined with an alcohol compound and subjected in the presence of an acid catalyst to the esterification of the maleinamic acid with the alcohol compound for the production of a maleinamic ester in a high yield. Thus, this invention allows a maleinamic ester of high purity to be produced expeditiously and economically from maleic anhydride as the starting material without requiring the maleinamic acid produced as an intermediate to be separated for the refinement of the reaction solution.

We claim:

1. A method for the production of a maleinimide, characterized in that the production is attained by heating a maleinamic ester compound represented by the general formula (1):

wherein $R^1$ is an alkyl group of 1 to 8 carbon atoms or a cycloalkyl group of 3 to 8 carbon atoms, in an inert organic solvent in conjunction with a mono(cyclo) alkyl sulfuric acid represented by the general formula (2):

wherein $R^2$ is an alkyl group of 1 to 8 carbon atoms or a cycloalkyl group of 3 to 8 carbon atoms, at a temperature in the range of 20° to 200° C., thereby effecting a ring-closing alcohol-removing reaction.

2. A method as claimed in claim 1, wherein the concentration of alcohol in the reaction system is kept at a level of not more than 3% by weight.

3. A method as claimed in claim 1, wherein the amount of the mono(cyclo)alkyl sulfuric acid to be used is in the range of 0.01 to 2 moles per mole of the maleinamic ester.

4. A method as claimed in claim 1, wherein $R^1$ and $R^2$ are identical with each other.

5. A method as claimed in claim 2, wherein the amount of the mono(cyclo)alkyl sulfuric acid to be used is in the range of 0.01 to 2 moles per mole of the maleinamic ester.

6. A method for the production of a maleinimide, characterized in that the production is attained by heating a maleinamic ester compound represented by the general formula (1):

wherein $R^1$ is an alkyl group of 1 to 8 carbon atoms or a cycloalkyl group of 3 to 8 carbon atoms, in an inert organic solvent in conjunction with an acid catalyst at a temperature in the range of 20° to 200° C., thereby effecting a ring-closing alcohol-removing reaction.

7. A method as claimed in claim 6, wherein the concentration of alcohol in the reaction system is kept at a level of not more than 3% by weight.

8. A method as claimed in claim 6, wherein the amount of the acid catalyst to be used is in the range of 0.01 to 2 moles per mole of the maleinamic ester.

9. A method as claimed in claim 6, wherein the acid catalyst has deposited on a solid carrier at least one member selected from the group consisting of sulfuric acid, sulfuric anhydride, sulfonic acid, phosphoric acid, phosphorous acid, and hypophosphorous acid.

10. A method as claimed in claim 6, wherein the acid catalyst is at least one member selected from the group consisting of phosphoric acid, phosphorous acid, and hypophosphorous acid.

11. A method as claimed in claim 7, wherein the amount of the acid catalyst to be used is in the range of 0.01 to 2 moles per mole of the maleinamic ester.

* * * * *